(12) United States Patent
Amin et al.

(10) Patent No.: US 8,930,341 B2
(45) Date of Patent: Jan. 6, 2015

(54) MOBILE COMMUNICATIONS DEVICE WITH ELECTRONIC NOSE

(71) Applicants: Alexander Himanshu Amin, Solon, OH (US); Himanshu Subhash Amin, Solon, OH (US)

(72) Inventors: Alexander Himanshu Amin, Solon, OH (US); Himanshu Subhash Amin, Solon, OH (US)

(73) Assignees: Alexander Himanshu Amin, Solon, OH (US); Himanshu Subhash Amin, Solon, OH (US)

( * ) Notice: Subject to any disclaimer, the term of this patent is extended or adjusted under 35 U.S.C. 154(b) by 0 days.

(21) Appl. No.: 14/219,914

(22) Filed: Mar. 19, 2014

(65) Prior Publication Data

US 2014/0201182 A1 Jul. 17, 2014

Related U.S. Application Data

(63) Continuation-in-part of application No. 13/839,206, filed on Mar. 15, 2013.

(60) Provisional application No. 61/643,781, filed on May 7, 2012.

(51) Int. Cl.
*G06F 7/00* (2006.01)
*G06F 17/30* (2006.01)
*G01N 33/00* (2006.01)

(52) U.S. Cl.
CPC ...... *G06F 17/30477* (2013.01); *G01N 33/0031* (2013.01)

USPC .......... 707/706; 707/736; 707/741; 707/754; 707/758

(58) Field of Classification Search
CPC .................... G06F 17/30001; G06F 17/30023; G06F 17/30283; G06F 17/30861; G06F 17/30864; G06F 17/30867; G06F 17/30997
USPC .................. 707/705, 706, 736, 741, 754, 758
See application file for complete search history.

(56) References Cited

U.S. PATENT DOCUMENTS

| | | | |
|---|---|---|---|
| 6,532,801 B1 * | 3/2003 | Shan et al. ...................... | 73/40.7 |
| 7,827,189 B2 * | 11/2010 | Hayama ........................ | 707/758 |
| 2001/0045953 A1 * | 11/2001 | Staples ........................ | 345/440 |
| 2008/0262743 A1 * | 10/2008 | Lewis et al. ...................... | 702/19 |
| 2010/0131206 A1 * | 5/2010 | Angell et al. .................... | 702/23 |
| 2011/0184740 A1 * | 7/2011 | Gruenstein et al. ........... | 704/275 |

* cited by examiner

*Primary Examiner* — Hares Jami
(74) *Attorney, Agent, or Firm* — Amin, Turocy & Watson, LLP

(57) ABSTRACT

Systems and methods for a mobile electronic system that gathers and analyzes odors, airborne chemicals and/or compounds. A signature or representation of the odors, airborne chemicals and/or compounds can be generated. Extrinsic data associated with the odors, airborne chemicals and/or compounds or capturing the odors, airborne chemicals and/or compounds can be identified. A model can be generated based on the representation and the extrinsic data. Filters can be generated based on the extrinsic data. The model can be searched for candidate matches, solutions, or other results based on the representation and the filters. Results can be generated based on the search and candidate matches.

20 Claims, 13 Drawing Sheets

US 8,930,341 B2

MOBILE COMMUNICATIONS DEVICE WITH ELECTRONIC NOSE

PRIORITY CLAIM

This patent application is a continuation-in-part (CIP) of U.S. patent application Ser. No. 13/839,206, filed on Mar. 15, 2013, entitled MOBILE COMMUNICATIONS DEVICE WITH ELECTRONIC NOSE, which claims the benefit of priority to U.S. Provisional Patent Application Ser. No. 61/643,781, filed on May 7, 2012, entitled ELECTRONIC NOSE SYSTEM AND METHOD. These patent applications are respectively incorporated herein by reference.

TECHNICAL FIELD

This disclosure relates to detection of chemical compounds, gases, and odor. More particularly to methods and systems for detection of chemicals or gases in air samples through a portable handheld device.

BACKGROUND

The proliferation, advancement, and affordability of electronic computing devices such as smart phones, laptop computers, personal computers, digital cameras, tablets, personal digital assistants (PDAs) and other electronic devices has made powerful electronic devices more available to the general public than ever before. Advancements in detection devices capable of odor detection, chemical detection and gas detection have made some detection devices common place in homes. For example, a sensor that can indicate presence of a chemical, gas or substance of interest can be useful to identify an unacceptable level of a toxic or explosive gas. There is an unmet need by the state of the art for convenient, rapid and reliable identification or detection of chemicals, gases, compounds, substances and the like.

SUMMARY

The following presents a simplified summary of the specification in order to provide a basic understanding of some aspects of the specification. This summary is not an extensive overview of the specification. It is intended to neither identify key or critical elements of the specification nor delineate the scope of any particular implementations of the specification, or any scope of the claims. Its purpose is to present some concepts of the specification in a simplified form as a prelude to the more detailed description that is presented in this disclosure.

Systems and methods disclosed herein relate to detection of odors, chemicals and gasses via handheld electronic devices (e.g., mobile phones). A sample delivery component is coupled to an electronic processor. The sample delivery component collects a headspace of a sample. The headspace is a portion of the sample that is to be analyzed. The sample delivery component can passively and/or actively collect the headspace of a sample by drawing air, for example.

A detection component is coupled to the electronic processor and sample delivery component. The detection component can analyze the headspace. The headspace analysis can determine presence and ratio of chemical, physical, and/or visual substances the make-up the headspace. Aspects of the detection component and the electronic processor can be coupled to a computer readable memory. The memory can store known analyzed samples of chemicals, gases, and/or odors, e.g., in the form of digital signatures, hash values, or any suitable use of identifying indicia or representation. The detection component can compare the analyzed headspace to known analyzed samples in the memory to determine the source of the headspace (e.g., flower, foodstuff, alcohol, perfume, etc.) and/or associate the analyzed headspace with a known source. In another example, when an analyzed headspace is determined to be a new combination of odors, gases, and/or chemicals, then the new combination of odors, gases, and/or chemicals can be stored in the memory.

In another embodiment, the detection component can determine if the headspace is a visual gas such as smoke without comparing the headspace to samples stored in memory. In this embodiment, the detection component can visually analyze the headspace.

In another embodiment, an image detection component (e.g., camera) can capture an image of a source of the headspace. The detection component can receive the captured image and determine the source of the headspace via analysis of the captured image, the analyzed headspace, or a combination thereof.

A display component displays can display a result of the analyzed headspace. The result can be a known source (e.g., type of flower, type of perfume, etc.). The result can comprise text and/or image. In one example, a result can be saved in memory and associated with as a new odor, gas, or chemical source.

The following description and the drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, and advantages of the present invention will be apparent upon consideration of the following detailed description, taken in conjunction with the accompanying drawings, in which like reference characters refer to like parts throughout, and in which.

DETAILED DESCRIPTION

Figure 1:
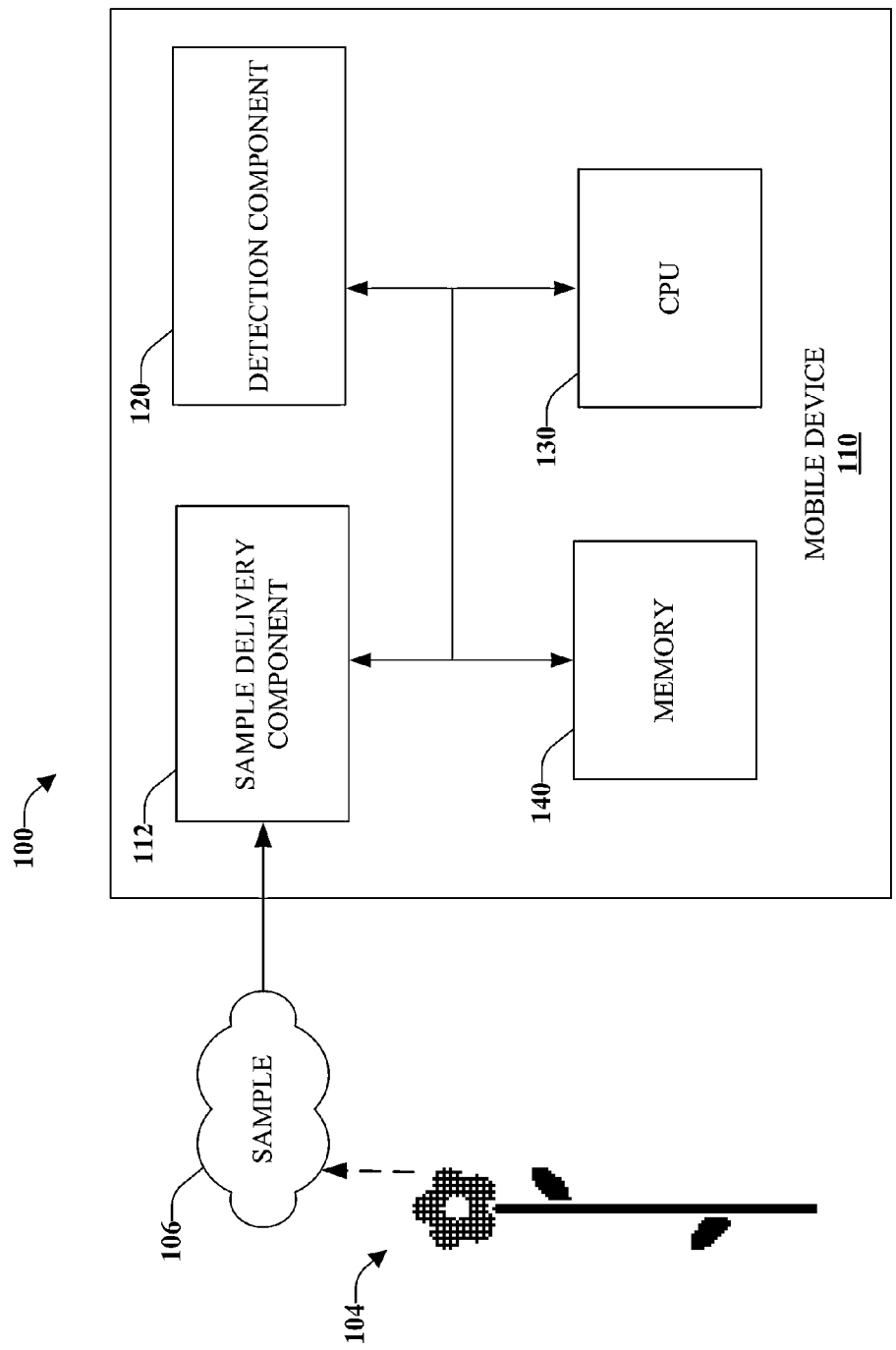
FIG. 1 illustrates a high-level functional block diagram of an example system comprising a mobile electronic nose device in accordance with various aspects disclosed herein.

Various aspects or features of this disclosure are described with reference to the drawings, wherein like reference numerals are used to refer to like elements throughout. In this specification, numerous specific details are set forth in order to provide a thorough understanding of this disclosure. It should be understood, however, that certain aspects of disclosure may be practiced without these specific details, or with other methods, components, materials, etc. In other instances, well-known structures and devices are shown in block diagram form to facilitate describing this disclosure.

Systems and methods disclosed herein relate to detection of odors, chemicals and/or gasses via handheld electronic devices. In one implementation, a mobile device receives, determines and identifies a source of a headspace of a sample. The mobile device is an electronic computing device such as for example a smartphone, tablet, PDA, laptop, cookware with circuitry, cooking utensils with circuitry, and the like.

In one embodiment, the mobile device passively receives a sample such as chemicals, gas, or odors. The sample can be received through openings in a body of the mobile device. In another embodiment, a mobile device actively draws in the sample via a sample delivery component. The sample delivery component can include an intake device such as a fan (e.g., bladed fan, airfoil fan, and the like), or a manually powered pump, for example. The intake device can pull air from outside the mobile device creating a positive pressure inside the device relative to the outside pressure. This causes air to pass through the device.

A detection component, coupled to a memory and a CPU, of the mobile device can receive a sample of the air. The detection component can analyze a headspace (portion) of the sample. The detection component can detect presence and amount of chemicals in the headspace. In one implementation, the detection component can include a sensory array. The sensory array can react to various chemicals within the headspace. The reaction can cause a change in physical or electrical properties of the sensory array. In one example, absorption of the chemicals in the headspace causes physical alterations of the various sensors in the sensory array. Each sensory array can react differently to the various chemicals. A CPU can transform the reactions of the sensory array into a digital signal. The digital signal can be computed based on a statistical model. For example, in one non-limiting embodiment, an organic ultra-thin transistor chemical sensor having a channel that consists of one or a few monolayers can be employed. The organic thin film transistor chemical sensors can have nearly monolayer thin film channels that act as highly-sensitive detectors of trace levels of organic vapors and can perform quantitative vapor analysis. The organic ultra-thin film can be permeable to a chemical analyte of interest.

A memory can store digital signals associated with sources (e.g., a rose, a foodstuff, burning foodstuff, etc.). In one embodiment, the detection component compares the digital signal associated with the headspace to the stored digital signals within the memory. The detection component can then find the best match and determine the source of the headspace. In another embodiment, the mobile device can compare the digital signal associated with the headspace to a memory of a server, such as a server connected via cellular communication networks, intranet, internet, or similar communication networks known in the art.

In another example, the detection component can determine that a best matched sample is not in memory. In this case, a new source is associated with the digital signal associated to the headspace. An input component can receive information about the source. The memory can store the associated source with the digital signal.

In another example, the mobile device can receive a plurality of headspaces associated with the same sample via the sample delivery component. The detection component can normalize the plurality of headspaces into a normalized headspace. The normalized headspace can be analyzed as above.

In another embodiment, input component can receive information about a source of a sample. In one example, the information can include text, location information (via global positioning satellites, user input, wireless access points, wired access points, etc.), audio information, and/or image information. The detection component can analyze the received information and the headspace to determine the source of the sample. In one implementation, the information received by the input component can narrow the possible sources to be associated with the headspace to be of a certain genus or type. For example, a voice capturing device can receive audio and determine that the audio contains a phrase such as "identify this flower". Thus, the detection component narrows the possible sources to flowers.

In another implementation, the detection component can detect if a food substance is expired, not expired, or the quality. For example, the detection component can determine if milk or wine has gone bad by comparing an analyzed headspace's associated digital signal to a known digital signal. In one aspect, input information can be received as text or audio information such as "is this wine spoiled?" and the detection component can reduce the amount of digital signals to compare to an analyzed headspace's digital signal.

In one example, the input component can include an image capturing device (e.g., a camera) can capture an image of a source associated with a sample and send the image to the detection component. The detection component analyzed the image of the source and the headspace of the sample associated with the source. The determination of the source can be enhanced and/or speed-up through the dual analysis of the captured image and the headspace. As one example, the captured image can narrow the possible sources of the headspace. For example, a sample of the fragrance of a flower can be received and an image of the flower can be captured. The detection component can determine the headspace is associated with a flower via analysis of the image of the flower.

Some non-limiting examples of types of sensors or detectors that can be employed in connection with identification of samples include: a calorimeter, a conductivity sensor, an enzymatic sensor, a biosensor, a chemical sensor, an Enzyme-Linked Assay sensor (e.g., an Enzyme-Linked Immunosorbent Assay (ELISA) sensor), an infrared (IR) spectroscopy sensor, a Nuclear Magnetic Resonance (NMR) sensor, an optical sensor, a permittivity sensor, a gas sensor, a Radio Frequency (RF) sensor, an electronic tongue sensor, a multi-frequency RF sensor, a cantilever sensor, an acoustic wave sensor, a piezoelectric sensor, a responsive polymer-based sensor, a quartz microbalance sensor, a metal oxide sensor, an X-ray Fluorescence (XRF) sensor, a nucleic acid-based sensor (e.g., a DNA-, RNA-, or aptamer-based sensor), or a regenerable sensor.

Furthermore, it is to be appreciated that multiple modalities can be employed in connection with converging on identification of a sample. For example, image or video capture components of a mobile device can be employed to identify item(s) of interest to be analyzed, audio analysis, voice analysis, text, can be employed in connection with determining identification goals of a user as well as determining properties of items that are analyzed. A user can take an image of an item (e.g., a snack) and utter, "is this allergen safe?" The image can be analyzed (e.g., using pattern recognition) to identify that it is a cookie as well as likely type of cookie (e.g., peanut butter). Based on the utterance, the system determines that the user is interested in ensuring that the cookie does not include items that may cause an allergic reaction (e.g., nut allergy). The electronic nose can be employed to detect presence of nuts in the cookie or any other potential allergen that might affect the user. Accordingly, the combination of pattern, voice and smell detection can provide a higher confidence level regarding item and goal determination as compared to using just one sensing modality.

Moreover, geographic location, time of day, season, etc. can also be employed in connection with facilitating identification. For example, a global positioning system (GPS) component of the mobile device can provide geographic location, and such information coupled with temporal or season information can facilitate factoring likelihood of gases, chemicals, substances, compounds, allergens or the like that have a high or low probability of presence at such location and time. If the mobile device is located in Ohio during the month of May, likelihood of certain allergens (e.g., tree and grass pollens) can be factored into a determination of presence of certain items of interest Likewise, if the mobile device is located in the Arctic Circle, and the device is located outside the likelihood of a live plant or animal being a source of an item is relatively low. In yet another example, identification of location within a particular restaurant can also be employed to facilitate item identification. If the restaurant is an Indian restaurant as compared to a steak house, the presence of certain exotic spices (e.g., turmeric, saffron, garam masala, cumin, coriander, etc.) is likely to be higher than in the steak house.

Embodiments disclosed herein can leverage multiple modalities (e.g., image or pattern recognition, location based services, web-based search tools, electronic noses, chemical sensors, audio recognition, time, date, season, location, etc.) to facilitate converging on user item identification goals as well as item identification.

Sensors can be self-cleaning (e.g., vibration, light, chemical or gas washes, etc.) as well as disposable.

In the smelling process of the human olfactory system, the initial step is to bind specific odorants to the olfactory receptor protein that triggers signal transduction in a cell. Olfactory receptors expressed in the cell membranes of olfactory receptor neurons are responsible for the detection of odorant molecules. That is, when the odorants bind to the olfactory receptors as described above, the receptors are activated. The activated olfactory receptors are the initial player in a signal transduction cascade, which ultimately produces a nerve impulse, which is transmitted to the brain. These olfactory receptors are members of the class A rhodopsin-like family of G protein-coupled receptors (GPCRs). In accordance with an embodiment, an olfactory receptor-functionalized transistor is provided, that is useful for a bioelectronic nose which can detect and analyze specific odorants with high selectivity, by functionalizing a nanostructure transistor with an olfactory receptor (e.g., a lipid membrane having an olfactory receptor protein is formed to cover surfaces of a source electrode, a drain electrode, and a nanostructure).

The olfactory receptor protein belongs to a family of G-protein coupled receptors and may exist over the surface of, the interior of, or the surface and interior of a lipid double membrane. An olfactory receptor membrane generally includes an ionizable cysteine residue and exists in a conformational equilibrium between biophysically activated and non-activated states. The activated and non-activated states of the olfactory receptor molecule are associated with a negatively-charged base form and a neutral acid form of cysteine, respectively. When specific odorants bind to olfactory receptor molecules, equilibrium of receptor molecules moves to an activated receptor form having negative charges. The negative charges of the olfactory receptor molecules which were changed into an activated state modulate contact resistance between metal electrode and nanostructure, leading to reduction in conductance. In accordance with an embodiment, odorant molecules can be detected highly selectively based on electrostatic perturbation of a nanostructure junction generated from a conformational change by binding odorants to olfactory receptor molecules. Thus, highly-specific detection of odorants with femtomolar sensitivity can be achieved in real time, and various and novel applications such as a highly selective artificial nose application can be achieved. In one embodiment, the nanostructure may be at least one form selected from the group consisting of nanotube, nanowire, nanorod, nanoribbon, nanofilm, and nanoball. For example, semiconductor nanowires such as silicon nanowires, and carbon nanotubes may be used, and a single-walled carbon nanotube can provide desirable high biocompatibility and device characteristics.

In another embodiment, a random network of single-walled carbon nanotubes (SWCNTs) coated with non-polar small organic molecules in conjunction with learning and pattern recognition algorithms (e.g., artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor) can be employed. For example, detection of volatile compounds as biomarkers for diagnosis of medical conditions can be performed using olfactometry systems that perform odor detection through use of an array of cross-reactive sensors in conjunction with pattern recognition algorithms. Each sensor can be widely responsive to a variety of odorants. Each analyte can produce a distinct signature from an array of broadly cross-reactive sensors. This configuration allows to considerably widen the variety of compounds to which a given matrix is sensitive, to increase degree of component identification and, in specific cases, to perform an analysis of individual components in complex multi-component mixtures. Pattern recognition algorithms can then be applied to the entire set of signals, obtained concurrently from a set (e.g., one or more) of sensors in the array, in order to glean information on identity, properties and concentration of vapor exposed to the sensor array.

In one or more embodiments, a smell or scent can be identified based on a unique vibration signature. For example, a micro spectrometer can be employed to measure a vibration signal of received or gathered molecules or particles, such as molecules of a headspace. A micro spectrometer can analyze gas or molecules using spectrometry and identify particles therein at a very granular level, the spectrographic signature can be matched to database of known scent signatures to identify scent associated with the sample. Additionally, the signature can be fed into a trained machine learning system (MLS) to perform the scent determination.

According to the vibrational theory a smell of a molecule is determined by intramolecular vibrations (frequency and amplitude), rather than by the shape of the molecule. Thus, a micro spectrograph can be utilized to determine vibrations of molecules within a headspace. The vibrations can be cross referenced with kwon vibrations to identify gases or molecules with the headspace.

Referring now to FIG. 1, there is illustrated a non-limiting exemplary implementation of a system 100 in accordance with various aspects of this disclosure. The system 100 can include mobile device 110 that can include a sample delivery component 112, a detection component 120, a computer processing unit (CPU) 130, and a memory 140. The mobile device 110 provides for gathering samples, and detecting and identifying source of a sample. The mobile device 110 receives sample 116 associated with a source 114. Sample 116 can be an odor, chemical, and/or airborne fragrance given off by source 114. In one aspect, CPU 130 is capable of executing various components and/or portions of components stored in a computer readable memory 140.

In some embodiments, sample delivery component 112 and/or detection component 120 can be modularly connected with mobile device 110. For example, a sample delivery component 112 can be comprised in a modular device that can communicatively connect or couple with mobile device 110 (e.g., via an interface, such as a universal serial port (USB), Micro USB, Mini USB, Lightning™ port, Bluetooth™, etc.). In another aspect, a modular devices can be removably connected to mobile device 110, such as through a locking mechanism (e.g., latch, clip, etc), magnetic connection, Velcro™ connection, threaded connection, or other various forms of connection.

The sample delivery component 112 can receive the sample 116. In one implementation, the sample delivery component 112 passively receives the sample 116 as the sample 116 diffuses. In another implementation, the sample delivery component 112 actively gathers the sample 116. For example, sample delivery component 112 can comprise an intake component that draws air into the mobile device 110 or a portion of the mobile device by creating a negative air pressure in the mobile device 110 or the portion of the mobile device relative to an external air pressure.

The sample delivery component 112 is in fluid communication with the detection component 120. Detection component 120 can receive the sample 116 and analyze a headspace of the sample 116. Detection component 120 can analyze the chemical composition of the headspace or analyze a visual aspect of the headspace.

In one implementation, detection component 120 includes a sensory array. The sensory array can comprise an array of polymer films, each polymer film of the array of polymer films can be of a slightly different type. However, it is to be appreciated that various polymer films of the array of polymer films may be of a same type. The electrical conductivity of the different types of films varies in the presence of different chemicals, so that when the array of films is exposed to a particular odor, the different films respond in a characteristic way. In another aspect, an array of polymers can respectively swell to varying levels when exposed to different molecules of a headspace. An aggregate amplitude signals associated with the polymers can generate a result as a unique signature for a particular smell. It is noted that the polymer films can be removable or replaceable (e.g., disposable). For example, a cartridge can be removed and a new cartridge can be inserted into the detection component 120.

In an example, detection component 120 can determine when a polymer film should be replaced. In an aspect, determining when to replace the polymer film can be based on passage of time, a number of scents smelled, a number of attempts to smell scents, degradation in accuracy, and the like.

In another implementation, detection component 120 can include a micro spectrometer that can analyze particles to identify the particles or determine concentration of different particles. It is noted that an identified particle or combination of particles can represent a scent. A signature can be generated from the combination of particles and can be utilized to identify a source.

In some embodiments, a user can provide a known scent to filer from a headspace. For example, a gathered headspace may contain a scent known by the user and a scent unknown by the user. The detection component 120 can remove the known scent to identify the unknown scent or generate a representation of the unknown scent.

In another example, the sensory array can comprise an array of transistors made out of various semiconductor materials (e.g., silicon oxide sensor). Transistors made of different materials can respond differently to different chemicals, so that the array produces a distinctive signal when exposed to an odor.

In another implementation, the detection component 120 can include visual detectors (e.g., a photoelectric detector). Visual detectors can comprise a light source and a light sensor. The light source produces a light that is aimed at the light sensor. The light sensor can determine when the light is blocked. It is to be appreciated that the detection component can comprise one or more sensors. Further, the sensors can comprise various sensors such as ionization sensors.

Detection component 120 converts the reactions of the sensory array or the visual system into a digital signal. The digital signal represents a chemical composition of the headspace. The memory 140 can store the digital signal. The detection component 120 can compare the digital signal to various other digital signals stored in memory 140 to determine an identity of a source associated with the headspace. In one implementation, detection component 120 uses at least one of a hash table, fuzzy logic, artificial neural network (ANN), or pattern recognition modules, for example, to determine an identity of a source associated with the headspace.

In an embodiment, detection component 120 can train a machine learning system to identify smells (e.g., sources of a sample). In an aspect, a model can be trained using any number of samples that are analyzed by humans. For example, users can provide input identifying a source of a sample. For iterations of a user identifying a smell, the smell can be stored in one or more databases. The iterations can be utilized to train a model (e.g., generate a library of smells). The model can increase in size, robustness, and/or accuracy as user input increases. In an aspect, a number of identifiable smells (e.g., representations of samples match with a source) can continue to grow indefinitely.

In one or more embodiments, an initial model can be a pre-trained or seeded model that, once launched on a local device (e.g., mobile device 110), can continue with its training on a per user/device basis. In an aspect, the model can be customized per owner. It is noted that a customized (e.g., per user or group of users) model can be stored locally or remotely (e.g., cloud based storage. In some embodiments, a local model data (e.g., of mobile device 110) can be shared with a server to enhance a server model/library. It is noted that a user can provide input to opt-out of sharing a model.

Figure 2:
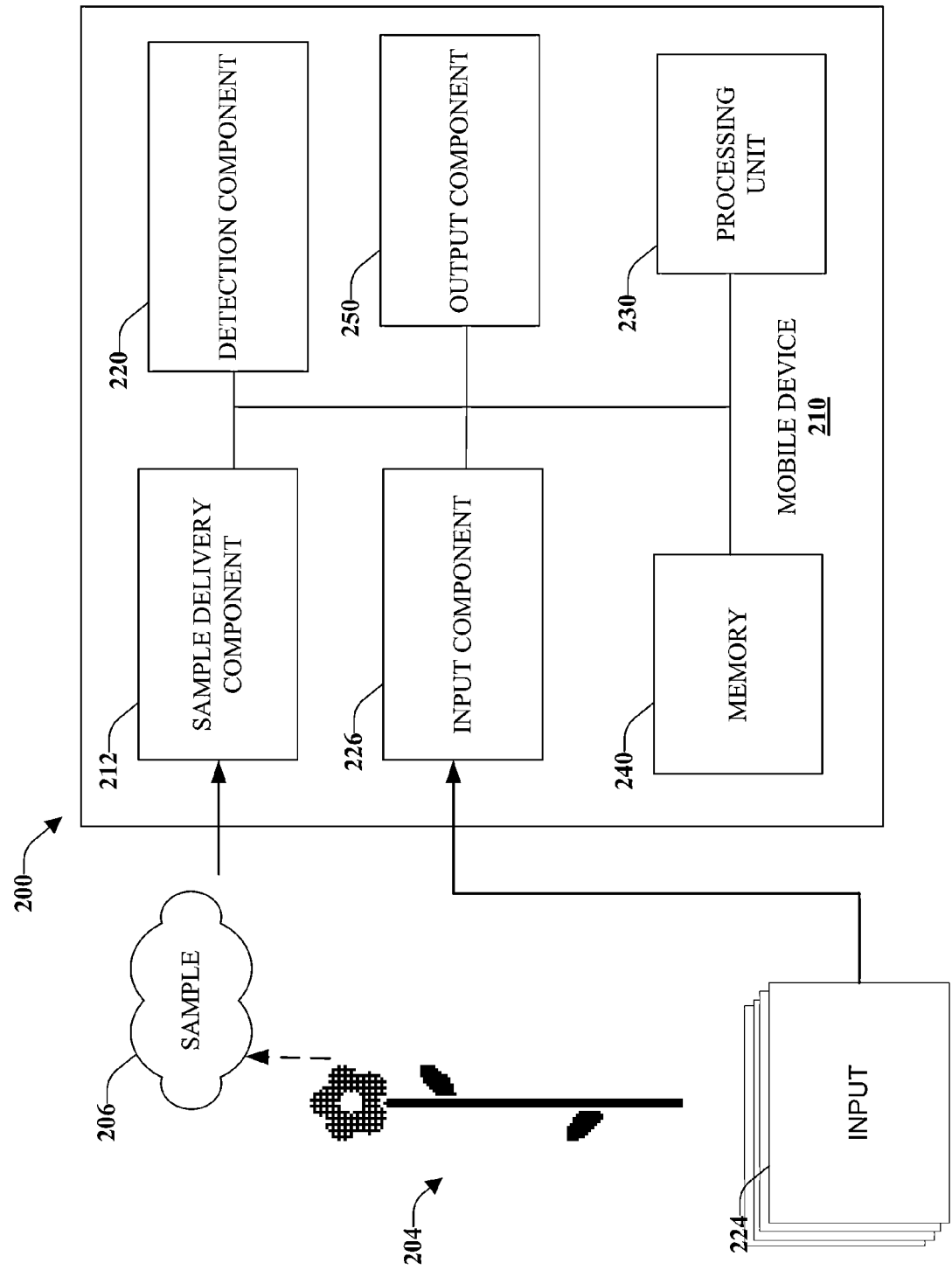
FIG. 2 illustrates a high-level functional block diagram of an example system comprising a mobile electronic nose device including an input component and an output component in accordance with various aspects disclosed herein.

Now turning to FIG. 2, there illustrated is a non-limiting exemplary embodiment of a system 200. System 200 can comprise a mobile device 210 capable of using input 224 to aid in detecting and/or identifying various odors, chemical compounds, aromas, and or gaseous substances. Mobile device 210 comprises a sample delivery component 212, a detection component 220, an input component 226, a computer processing unit (CPU) 230, an output component 250 and a memory 240. Mobile device 210 provides for receiving a sample 206 and detecting or identifying a source 204 associated with sample 206. In one aspect, sample 206 is a portion of air in the proximity of mobile device 210. In another aspect, sample 206 can contain a scent, an odor, chemical(s), airborne particles, or gaseous substance(s).

In one aspect, CPU 230 is capable of executing various components and/or portions of components stored in a computer readable memory 240. Memory 240 can also store a plurality of entries, each entry comprising a digital odor signals, class, and source name, for example. Each entry can also comprise various other fields such as photo identification, date detected, and location, to name a few.

Sample deliver component 212 can actively or passively receive sample 206. Detection component 220 can receive a headspace of sample 206 and analyze the headspace. Detection component 220 can determine a digital odor signal associated with the headspace.

Input component 226 can receive and analyze input 224. Input component 226 can receive input 224 that can comprise extrinsic data, such as audio, visual, text, location data, and/or other user input. In one aspect, input component 226 includes one or more input interfaces such as a microphone, a camera, a key board, an actuator, a touch screen and/or other user interfaces capable of receiving input 224, for example. In one aspect, input component 226 can receive input 224 relating to source 204 and/or sample 206. For example, input 224 can contain information relating to a source's class, image, and/or location.

In one implementation, input component 226 comprises a microphone. Input component 226 receives input 224 as audio information via the microphone. Input component 226 can identify speech in input 224. Memory 240 can store the digital signal. For example, a user can say "identify this flower" and input component 226 can receive the audio as input 224. In one example, input component 226 can convert the audio to a digital signal and analyze the digital signal. In the above example, a filter can be generated to limit possible results to flowers. The filter can facilitate searching of a specialized model and/or a portion of a model that is associated with flowers. Limiting searching of the specialized model (or portion of a larger model) can result in a more accurate result and/or a faster searching/identification process.

The audio can be utilized by detection component 220 to generate a command and/or extrinsic data associated with receiving a sample. For example, detection component 220 can identify a phrase such as "identify," "analyze," "add scent," and the like. The phrase can correspond to one or more commands. In an example, if a user knows an identity of source 204, the user can utter, "add this sent for a rose." Detection component 220 can determine that the source is a rose and can add the scent to a library or model. In another example, extrinsic data can be extracted from the audio. In the above example, the extrinsic data can be a type or classification of a source, such as a rose. In another aspect, a query can be generated based on the extract extrinsic data. For example, a filter can be generated to limit possible results to species of roses.

In another embodiment, input component 226 includes a user interface device, such as a touch screen or keyboard, for example. In one aspect, the user input device can receive input 224 as text. In another implementation, input 224 contains information relating to sample 206 and/or source 204. Detection component 220 can extract extrinsic data and/or commands from the text. The extrinsic data can be utilized to generate filters. For example, a user can provide the text "find a store where I can buy this perfume." A first filter can comprise "perfume" and can be utilized to limit possible results to perfumes. A second filter can comprise "stores" and can be utilized to generate a result that identifies stores where the perfume can be purchased. In one or more other examples, detection component 220 can determine a location of the mobile device 210. The location can be utilized as another filter that facilitates limiting possible results based on the location. In the above example, the identified stores can be stores within a determined distance from the location and/or online stores.

As another example, input component 226 can include a camera. The camera can capture visual information. The visual information can be received by input component 226 as input 224. In one aspect, the visual information is an image of source 204. Input component 226 can identification the image as relating to a class of objects, being a specific object, and the like. In one implementation, input component 226 determines if the image of source 204 is associated with an image stored in memory 240. For example, an image is captured and input component 226 determines if the image is an image of a flower. Determining a subject or object in an image can comprise utilizing pattern matching techniques. The pattern matching techniques can identify a type of object, an identity of the object, and the like. In some embodiments, a result of the pattern matching can be utilized as a filter that filters possible results.

Detection component 220 receives analyzed input from input component 206. The analyzed input can contain extrinsic information relating to source 204, sample 206, receiving the sample 206, and the like. Detection component 220 applies the analyzed input to narrow and/or improve identification of source 204 associated with sample 206. For example, detection component 220 receives analyzed input containing information such as "flower" and then detection component 220 can compare the analyzed headspace to entries in memory 204 that have a class type of "flower". Detection component 220 can limit its comparison of the digital headspace signal to entries in memory with a class association of "flower". In another example, a filter can be generated to filter possible results and the filter can be transmitted to a search engine (and/or utilized to generate a query to a search engine).

In another aspect, detection component 220 can receive input 224 or analyzed input from input component 206 that contains a plurality of information relating to a source 204 and/or sample 206. For example, input 224 can contain extrinsic data such as a date field, a location field, and an image field. In one aspect, input 224 can contain a date field and location field. Entries in memory 240 can have associated date ranges and location ranges. Detection component 220 can apply the input 224 to limit searchable entries. For example, a flower may be indigenous to a certain location and may only bloom during a certain date range. Detection component 220 can apply input 224 to reduce the number of possible entries.

In an embodiment, detection component 220 can utilize extrinsic information to reduce a number of possible results (e.g. sort known scents). As noted supra, extrinsic information can include locations, GPS coordinates, seasons (e.g., season of a year), time, date, user input (e.g., voice, text, etc.), images, and the like. The extrinsic information can be utilized to hone in on a match of a collected sample and the like. In an example, a user can provide a voice command, textual query, or the like that indicates that the user desires to identify a scent based on a species associated with a source. Detection component 220 can then limit a search to a set of candidate scents belonging to the desired species. In another aspect, detection component 220 can further limit candidate scents based on additional extrinsic information not provided by a user but rather automatically gathered by detection component 220. For example, detection component 220 can determine a current location (e.g., a restaurant), date, and time and can apply the current location, date, and time to further limit potential candidate scents.

In another example, a user can provide a command "identify this vegetable dish." Detection component 220 can determine that the species is one or more of food or vegetables. Detection component 220 can further determine that the user is in an Italian restaurant (e.g., based on GPS location, a local access point, other devices, etc.) during the month of August. Thus, potential candidate scents can be further limited based on dishes common to Italian restaurants (or dishes offered by the particular restaurant) and having a vegetable that is available during August. In another aspect, an image of the dish can even further limit potential candidate scents. It is noted that the above is but a limited set of examples; as such, detection component 220 can utilize virtually any criterion (extrinsic data) or combination of criteria to limit candidate scents, improve accuracy, decrease processing time, or otherwise alter performance.

As another example, a user can identify a smell and system 200 can collect a headspace, perform an analysis (e.g., locally or through a cloud-based analysis), and apply filters to facilitate generation of a search query. The search query can be transmitted to a search engine to generate a result. The result can comprise an identification of sources, scent signature matches, confidence scores, solutions/cures, background information of sources, and the like. In some embodiments, a search engine (e.g., utilizing one or more models) can generate a confidence score and provide the confidence score to a user (e.g., 99% confident that a scent includes garlic and onion).

In one or more embodiments, system 200 can be configured to perform specialized functions or limited detection of substances. In an aspect, system 200 can be pre-configured to identify a number of scents. In another aspect, system 200 can apply constraints (e.g., via sample delivery component 212 or detection component 220). For example, detection component 220 can be configured to limit a number of possible substances based on a detection mode. As described herein, detection modes can comprise one or more of a "dangerous substance mode," "hunting mode," "allergy mode," "breath mode," "cooking mode," or the like.

For example, in a dangerous substance mode, detection component 220 can limit searchable substances (e.g., representations of substances) to a defined list of substances, such as carbon monoxide, smoke, other harmful gases, toxins, etc. In an aspect, a dangerous substance mode can be triggered based on user input (e.g., manually entering the mode) or automatically (e.g., based on a trigger). For example, a dangerous substance mode can be triggered during certain times of day (e.g., such as at night when a user typically sleeps), based on current locations (e.g., while in a car, boat, a garage, next to a bed, etc.), based on a charging status of mobile device 210 (e.g., users typically charge a phone in and stay near the phone), and the like.

In an allergy mode, system 200 can be configured to identify a limited number of sources that a user is allergic to, potentially allergic to, or otherwise adverse to. For example, a user can provide input identifying that the user is allergic to nuts. In an allergy mode, detection component 220 can limit a number of searched headspaces to headspaces associated with nuts. It is noted that the allergy mode can be triggered manually or automatically. For example, a user can provide input to trigger the allergy mode to detect presence of an allergen. In another example, a user may experience an allergic reaction (e.g., from food, seasonal, dust, etc.) and not know the cause of the allergic reaction. The user can trigger the allergy mode to facilitate detection component 220 identifying a source associated with a headspace and providing a list of possible allergens. In accordance with various embodiments disclosed herein, detection component 220 can store identified sources and compare the identified sources to determine a common possible allergen. In another example, detection component 220 can utilize extrinsic information (e.g., location, date, time, etc.) to determine the possible allergens.

As another example, system 200 can be configured to facilitate performance of a "breath mode." In a breath mode, detection component 220 can discern a level of bad or good breath. In an aspect, a level of bad or good breath can be based on subject analysis or objective analysis. Subjective analysis can comprise an analysis based on user input or historical data indicative of past user input or actions. Objective analysis can comprise an analysis based on heuristics such as identification of particular headspaces, analysis of concentration of a particular odor, or the like. In an aspect, a user can provide input to train a model, such as breathing when a level of good or bad breath is known and providing input identifying the level of good or bad breath. As above, other extrinsic information can be utilized to determine a level of good of bad breath. For example, during a first time period (e.g., morning hours) the breath mode can analyze a headspace to determine whether a coffee odor is present. It is noted that a user can trigger a breath mode based on interaction with an interface (e.g., button, touch screen, voice command), breathing into or about mobile device 210 (e.g., a microphone can detect the user breathing into the mobile device), and the like.

In another example, system 200 can be configured to facilitate performance of the breath mode to diagnose a user. For example, in breath mode, a user can breathe into sample delivery component 212 and detection component 220 can discern a blood sugar level, such as based on a presence or concentration of ketones (e.g., acetone). Ketones levels increase when there is insufficient amounts of insulin to drive cells. Typically, diabetics exhibit higher levels of ketone accumulation and ketone levels in a user's breath can be correlated to blood glucose levels.

In some embodiments, detection component 220 can generate alerts or suggestions based on a triggering event. For example, detection component 220 can detect a sneeze or other trigger and can perform a search of a headspace to identify potential causes of the sneeze or other trigger. In an example, detection component 220 can search a headspace for the presence of dander, pollen, representations of plants, and the like to facilitate a possible cause of the sneeze. An alert can be generated to inform a user of the presence of an identified source and offer a possible correlation, such as the user may be allergic to cats. In some embodiments, system 200 can include a photo sensor that can identify a level of light and/or change in a level of light. If a change in lighting is detected, detection component 220 can determine that the change in light may be a cause of a sneeze. In another aspect, detection component 220 can generate an output identifying possible causes and allow the user to select a possible cause.

In various embodiments, detection component 220 can determine a solution, warning, suggestion, or other descriptive data associated with a scent based on identification of substances and/or extrinsic information. For example, a user can take a picture of source and/or utter a command to identify the chemical makeup of the source (e.g., snaps a picture of a blade of a weed and utters identify this weed). The combination of pattern recognition coupled with headspace analysis can facilitate identifying accurately the type of plant as well as provide supplemental information regarding allergic properties, best ways of eradicate the weed, potential harmful or beneficial properties, or the like. In another embodiment, detection component 220 can detect a substance and provide a potential solution. For example, radon gas, leaking oil or gas, or other chemicals, body odor, foot odor, type of bacteria associated with particular odors can be detected and solutions to kill such bacteria can be generated.

An alert can be generated based on a concentration, degree, or presence of a substance, such as an airborne pathogen. For example, detection component 220 can determine a level or concentration of an airborne pathogen based on an analysis of a headspace. If the pathogen has a high concentration (e.g., above a certain threshold) the system 200 can alert a user to prevent developing an illness or sickness (e.g., the flu). In some embodiments, system 200 can share locations of high concentrations of airborne pathogens. The shared locations can facilitate generation of a map of known high concentrations. In an aspect, as multiple systems share locations, a map can be updated and enhanced. In another aspect, the map can be utilized to alert a user who is heading towards an area (e.g., location) identified as being associated with a high concentration of an airborne pathogen.

It is noted that the system 200 can identify scents and the relative concentration of respective sources (e.g., 75% roses, 10% lilac, 5% honeysuckle, and 10% miscellaneous or unknown sources) through analysis of a headspace. For example, detection component 220 can analyze a headspace and determine whether one or more sources are identified at least by a portion of the headspace. The detection component 220 can determine a concentration based on a ratio comparison of the headspace.

In another embodiment, detection component 220 can determine a direction of a scent and can determine a navigational path to a likely source of the scent. It is noted that detection component 220 can include an accelerometer, gyroscope, GPS component, or the like. In some embodiments, sample delivery component 212 can receive or gather multiple samples to determine a location or direction of a scent. For example, a user can walk in an environment and smell food, such as a barbeque scent, which the user desires to locate. Sample delivery component 212 can gather samples as a user moves and detection component 220 can determine whether a concentration of the scent is altered (e.g., increase or decreased). In one aspect, sample delivery component 212 can gather samples periodically (e.g., based on passage of time, distance traveled), randomly, semi-randomly, based on user commands, or the like. As samples are gathered and/or analyzed, the concentrations of a scent can be utilized to determine a direction for a user to travel in order to locate the scent. For example, if a concentration or intensity is increasing, the user may be traveling in the proper direction. In another example, a user can smell some foul odor in a building or other environment. The user can utilize mobile device 210 to detect the location of the foul smell and remove the smell (e.g., spoiled food, rotten garbage, and the like).

In other embodiments, other users can mark a location of the scent and, in response to detection component 220 detecting the scent, the location or source can determined based on the other users marking of the location of the scent. Once a location is determined, mobile device 210 can facilitate generating navigational directions to the location. It is appreciated that other extrinsic information can be utilized to identify a location or origin of a scent. For example, detection component 220 can determine scent is from a BBQ restaurant can look up or search for nearby restaurants serving BBQ food.

In an example, detection component 220 can facilitate identifying animals (e.g., prey or predators) in an area and inform a user or hunter of types of prey in the area (e.g., whitetail deer, wild boar, rabbit, turkey, ducks . . . ) or types of dangerous animals in the area (e.g., bears, wolves, etc.). As above, intensity of a scent and/or dander of an animal can be monitor such that the user can be guided to areas having greater intensity or concentrations. In one aspect, a threshold can be utilized to alert a hunter when an intensity is reached. For example, if a threshold is set to a high intensity the hunter can be alerted to signify the presence of an animal in a nearby vicinity. In another example, if the threshold is low, the hunter can be alerted that the animal may be moving or has left a vicinity. In some embodiments, detection component 220 can generate a scent marker that marks a location (e.g., GPS coordinates) of a particular scent, identified sources, and time-stamps the mark. The markers can be shared by other hunters and/or used to develop a map of animal trails and migration patterns. In another example, a hunter can capture an image of an animal track (e.g., via a camera), such as a footprint or hoof print, and detection component 220 can determine an animal associated with the track.

In another aspect, a particular source or scent can be filtered from a headspace. In an example, detection component 220 can detect one or more scents in a headspace. A particular scent can dominate or corrupt other scents. If the dominant scent is identified, it can be removed or filter to identify other scents. For example, exhaust fumes from a car can be identified and filtered from a headspace. In an aspect, filtering can include subtracting the representation of the exhaust fumes from a headspace. The residual scent can then be determined.

In another example, a user can provide input to identify a perfume and detection component 220 can detect the perfume and identify other descriptive information associated with the perfume. For example, information describing the perfume, a maker of the perfume, nearby location where the perfume can be found (e.g., such as a nearby retail store, an online store, and the like), a popularity of the perfume (e.g., based on a number of identifications associated with the perfume), or other information associated with the perfume.

Figure 3:
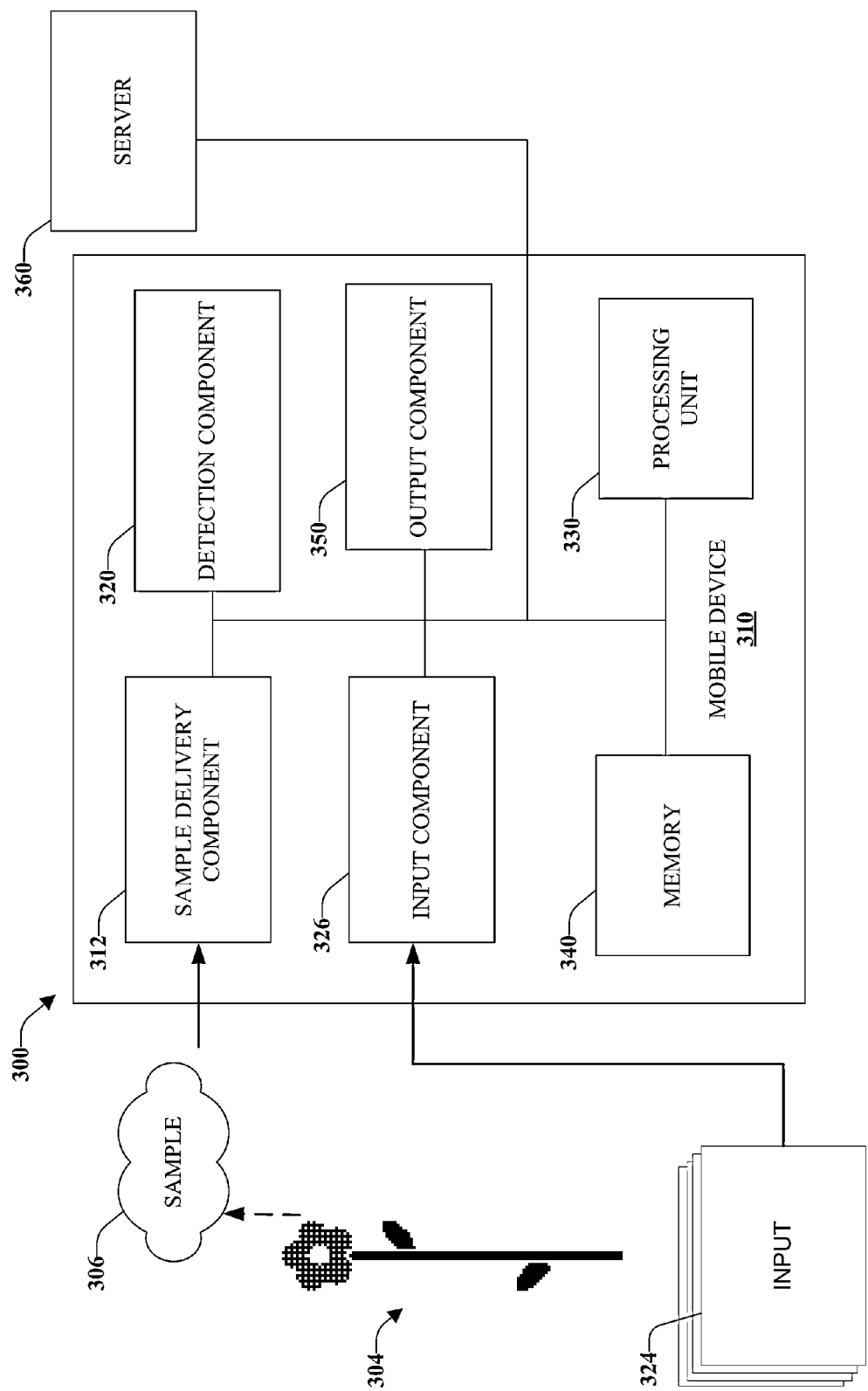
FIG. 3 illustrates a high-level functional block diagram of an example system comprising a mobile electronic nose device in communication with a server in accordance with various aspects disclosed herein.

Referring now to FIG. 3, there illustrated is a non-limiting exemplary embodiment of a system 300. System 300 can primarily comprise mobile device 310 in accordance with various aspects of this disclosure. Mobile device 310 comprises sample delivery component 312, detection component 320, input component 326, processing unit 330, memory 340, and output component 350.

Mobile device 310 can receive a sample 306 associated with a source 304 via a sample delivery component 312. Input component 326 can receive and analyze input 324 containing information relating to sample 306 and/or source 304. Detection component 320 can receive analyzed input and a headspace of sample 306. Detection component 320 can analyze the headspace in conjunction with the analyzed input.

In one aspect, processing unit 330 is capable of executing various components and/or portions of components stored in a computer readable memory 340. Memory 340 can also store a plurality of entries, each entry comprising a digital odor signals, class, and source name, for example. Each entry can also comprise various other fields such as photo identification, date detected, and location, to name a few.

In another aspect, mobile device 310 is in communication with one more server(s) 360. Communications can be facilitated via a wired (including optical fiber) and/or wireless technology. Server(s) 360 comprise one or more server data store(s) that can be employed to store information local to server(s) 360. In one implementation, server(s)'s 360 data store(s) contains one or more entries, each entry relates to unique sources with associated information, such as class, source name, digital identification, and image, for example.

In one implementation, detection component 320 receives entries and/or information relating to entries from server(s) 360. In another aspect, detection component 320 searches entries in server(s)'s 360 data store.

In another implementation, detection component 320 can send information relating to source 304 and or sample 306 to server(s) 360. Server(s) 360 can record information in the server data stores.

Output component 350 can output information. In one embodiment, output component 350 includes one or more output devices such as a speaker, and/or display. Output component 350 outputs information relating to sample 306, source 304 and a detection result. A detection result can include information relating to source 304 such as a determined identity and/or class.

In one or more embodiments, system 300 can utilize a cloud-based analysis or a local-based analysis of received data (e.g., a headspace). For example, sample 306 can be received by sample delivery component 310 and detection component 320 can generate a representation of the sample. A representation of the sample can be a spectrogram, a hash (e.g., based on a hash function), or the like. In some embodiments, system 300 can analyze the representation of the sample based on a locally connected database or library of representations of samples. In another aspect, input component 326 can receive a library of representations (or portion thereof) from server 360 or from another external storage device.

In another example, output component 350 can transmit a representation of a sample to an external device (e.g., server 360). The external device can analyze the representation of the sample, can transform the representation of the sample, and the like. For instance, a server can receive a representation of a sample and generate a hash of the representation. The server can then determine whether the hash corresponds to an entry in a hash table. If the hash does correspond to the entry, then data associated with the entry can be received by input component 326 and/or utilized to identify a source.

In embodiments, a sample can be analyzed in one or more phases, such as an initial analysis and a secondary analysis. As an example, mobile device 310 can perform an initial analysis that is constrained by one or more factors. The factors can include an amount of time (e.g., processing time), a number of entries in a local database, performance metrics of mobile device 310, and the like. For example, an initial analysis can be configures such that a result is generated within a predetermined time period. In another example, the initial analysis can be limited to a determined complexity based on a processing speed of processing unit 330. The secondary analysis can comprise a more detailed or stringent analysis. For example, the output component 350 can transmit a result of the initial analysis, a representation of the sample, and/or other data (e.g., user input, images, etc.) to server 360. Server 360 can perform a more detailed or stringent analysis to determine a source of the sample. In an aspect, the server 360 can compare the representation of the sample with a larger library of representations and the like.

In an implementation, mobile device 310 can share models (e.g., libraries) and/or utilize models in a cloud-computing environment. For example, mobile device 310 can share (e.g., transmit) a local library to other mobile devices or server 360. In an aspect, multiple libraries can be aggregated and a robust library can be generated. In some embodiments, a shared library can be based in part on extrinsic data such a location, date, time, and the like. For example, every time mobile device 306 gathers a sample, location data (e.g., GPS location, date, time, etc.) can be recorded and/or attached to a model. The location data can be matched with or location data to provide a more detailed and/or improved model.

In another aspect, detection component 320 can determine inaccuracies and/or anomalies within a model. For example, detection component 320 can cross-reference stored scents of a model with stored scents of one or more models. If detection component 320 determines that a representation of a sample matches another representation of a sample but identified sources do not match, then detection component 320 can mark the discrepancy for further analysis, generate a notification, correct the discrepancy, or otherwise process the discrepancy. In one example, detection component 320 can determine confidence scores associated different sources. A source having the highest confidence score can be chosen and the discrepancy can be resolved by replacing the source associated with the lower confidence with the source associated with the chosen confidence score. In another example, if a confidence score is not above a threshold confidence (e.g., 99%) and/or is not sufficiently greater than a confidence score associated with another source (e.g., 50% greater) then neither source is chosen. If neither source is chosen, entries in a model or library can be marked as entries needing additional data, entries having conflicting data, entries that are potential inaccurate, and the like.

In some embodiments, detection component 320 can identify a user identity as having a poor, advanced, or other level of sense of smell. For example, based on a history of scents and user input, detection component 320 can determine whether the user properly identifies scents. If the user has a threshold number of incorrect or inaccurate identifications, then the user can be identified as a user having a poor sense of smell. Entries of a model associated with a user having a poor sense of smell can be removed to increase accuracies of a model. In another aspect, a weighting system can utilize a level of sense of smell associated with users to generate a weighted score of entries associated with the users. For example, entries of a model associated with users having an advanced sense of smell can be given a greater weight than those associated with less advanced users.

In an example, mobile device 310 can utilize a specialized model that is trained by an expert, a set of experts, or other quality determining entities. Experts or quality determining entities can be focused along a certain field such as wine, spirits, perfumes, fruits (or foods in general), or any other field. For example, a set of experts can identify wines and quality associated with the wines. The qualities and scents can be utilized to train a model specifically designed to determine a quality of a wine. In another aspect, a specialized model may utilize In some embodiments, system 300 can share (e.g., via input component 326 or output component 350) identified scents and a review of a source associated with the identified scent. For example, a user can provide a review associated with the scent, such as a rating, "liking," text based review, or other input. The review can be transmitted and/or shared with other devices. In another aspect, user reviews can be utilized to train user generated models and/or generate leader boards associated with scents or particular fields of interest. For example, users, via mobile devices, can gather scents of a particular type of consumable product and votes for the products can generate leader boards.

Figure 4:
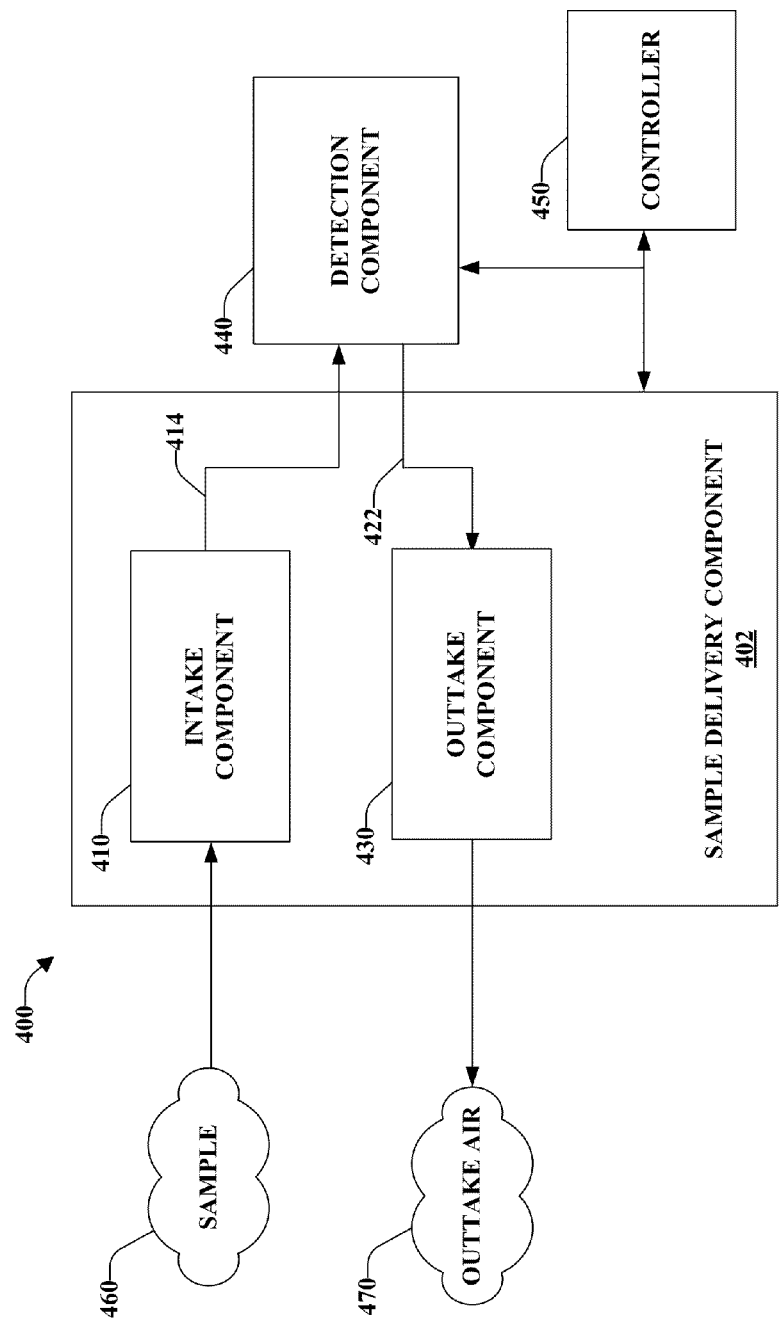
FIG. 4 illustrates a high-level functional block diagram of an example system comprising a sample delivery component in accordance with various aspects disclosed herein.

Referring now to FIG. 4, there illustrated is a system 400 which gathers a sample, delivers a sample, and/or removes a sample from a device in accordance with various aspects of this disclosure. Sample delivery component 402 can include am intake component 410, an intake line 414, an outtake line 422, an outtake component 430. A controller 450 can facilitate operation of sample delivery component 402 and various other components in accordance with this disclosure, such as detection component 440.

Intake component 440 gathers or receives a sample 460. In one aspect, intake component 440 passively receives sample 460 as sample 460 diffuses through airspace. In another aspect, input component 440 includes a mechanical device that can draw in sample 460. The mechanical device can include a bladed fan, a bladeless fan, or other known devices capable of drawing in air as known in the field.

In another aspect, intake component 410 can comprise one or more apertures in a mobile device. Sample 460 can enter the mobile device through the one or more apertures.

Intake line 414 can transfer or provide a passage to various components in accordance with this disclosure, such as detection component 440, for example. Intake line 414 can be in fluid communication with detection component 440, for example. Intake line 414 can comprise tubing, or other device of plastic, rubber, metal, or other suitable means as known in the art. Detection component 440 can analyze sample 460 or a headspace of sample 460.

Outtake line 422 can fluidly connect various components, such as detection component 440, to outtake component 430. Outtake Air 470 can pass through outtake line 422 and exit the mobile device through outtake component 430. Outtake component 430 can comprise one or more apertures to allow the spent sample 460 or other outtake air 470 to exit the mobile device.

In one aspect, outtake line 422 can comprise tubing, or other device of plastic, rubber, polymer, ceramic, metal, or other suitable means as known in the art.

In one implementation outtake component 430 can comprise a mechanical device for drawing a sample. The mechanical device can include a bladed fan, a bladeless fan, or other known devices (e.g., micro electro mechanical systems (MEMS) devices) capable of drawing in air as known in the field. For example, a system containing sensors and microjet MEMS actuators can be employed to exact some flow control, and synthetic jets can be employed to reduce drag and modify flow over air foils and bluff bodies. In one aspect, outtake component 430 and intake component 410 can each comprise one or more mechanical device. In another implementation, intake component 410 or outtake component 430 can utilize the same one or more mechanical devices. In another aspect, outtake component 430 can include a mechanical device that causes air to pass through input component 411 and output component 430.

In another implementation, outtake component 430 and intake component 410 can both utilize the same one or more apertures to allow air to enter and exit a mobile device.

Figure 5:
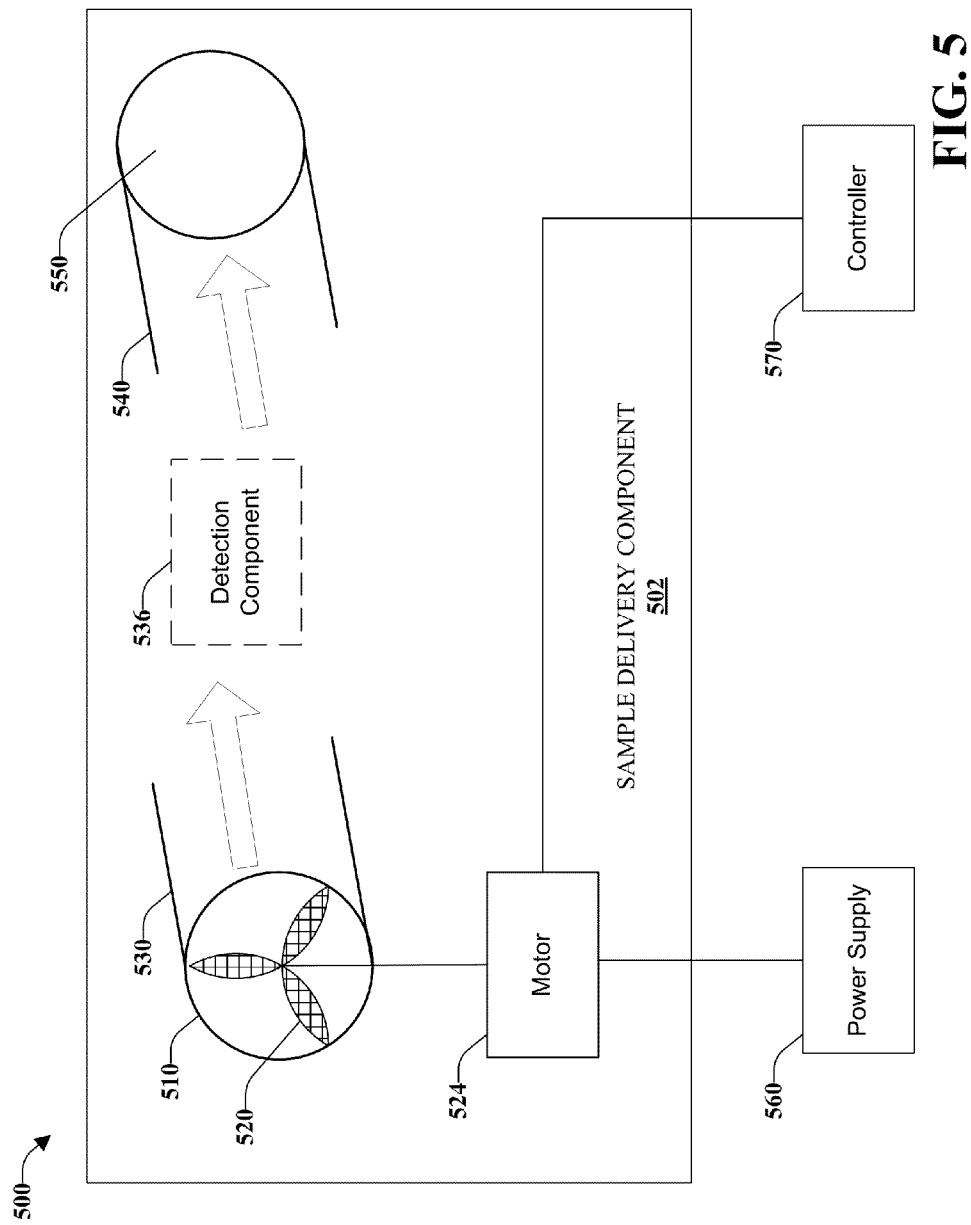
FIG. 5 illustrates an example schematic diagram of a system comprising a sample delivery component in accordance with various aspects disclosed herein.

Referring now to FIG. 5, there illustrated is a schematic diagram of an exemplary system 500 in accordance with various aspects of this disclosure. In accordance with various aspects of this disclosure, system 500 can comprise sample delivery component 502. Sample delivery component 502 can gather a sample in air space, deliver the sample to various components in a mobile device, and remove the gathered sample from the mobile device.

Sample delivery component 502 can comprise one or more intake apertures 510, fan 520, motor 524, intake duct 530, outtake duct 540, and one or more outtake apertures 550. A controller 570 can control various aspects of sample delivery component 502. Further, a power supply 560 can power various aspects of sample delivery component 502 such as fan 524, for example.

A sample can be received through one or more intake apertures 510. Fan 520 can draw in the sample. Likewise, motor 524 can receive power from power supply 560. As fan 520 rotates, it creates a low pressure area in the mobile device with respect to the airspace outside the device. Air is then caused to enter the one or more intake apertures 510.

The sample can pass through intake duct 530. Intake duct 530 can be in communication with various components, such as detection component 536. The sample can also pass through or be forces through outtake duct 540. The spent sample can then exit through one or more outtake apertures 550.

In other implementation, the intake duct 530 and outtake duct 540 can be of one unitary construction or modular construction. Likewise, power supply 560 can be a battery, fuel cell or other power source. Power supply 560 can be within sample delivery component 502 or can be a power supply for a larger mobile device. In another aspect, the one or more intake apertures 510 and one or more outtake apertures 550 can comprise the same one or more outtake apertures.

Figure 6:
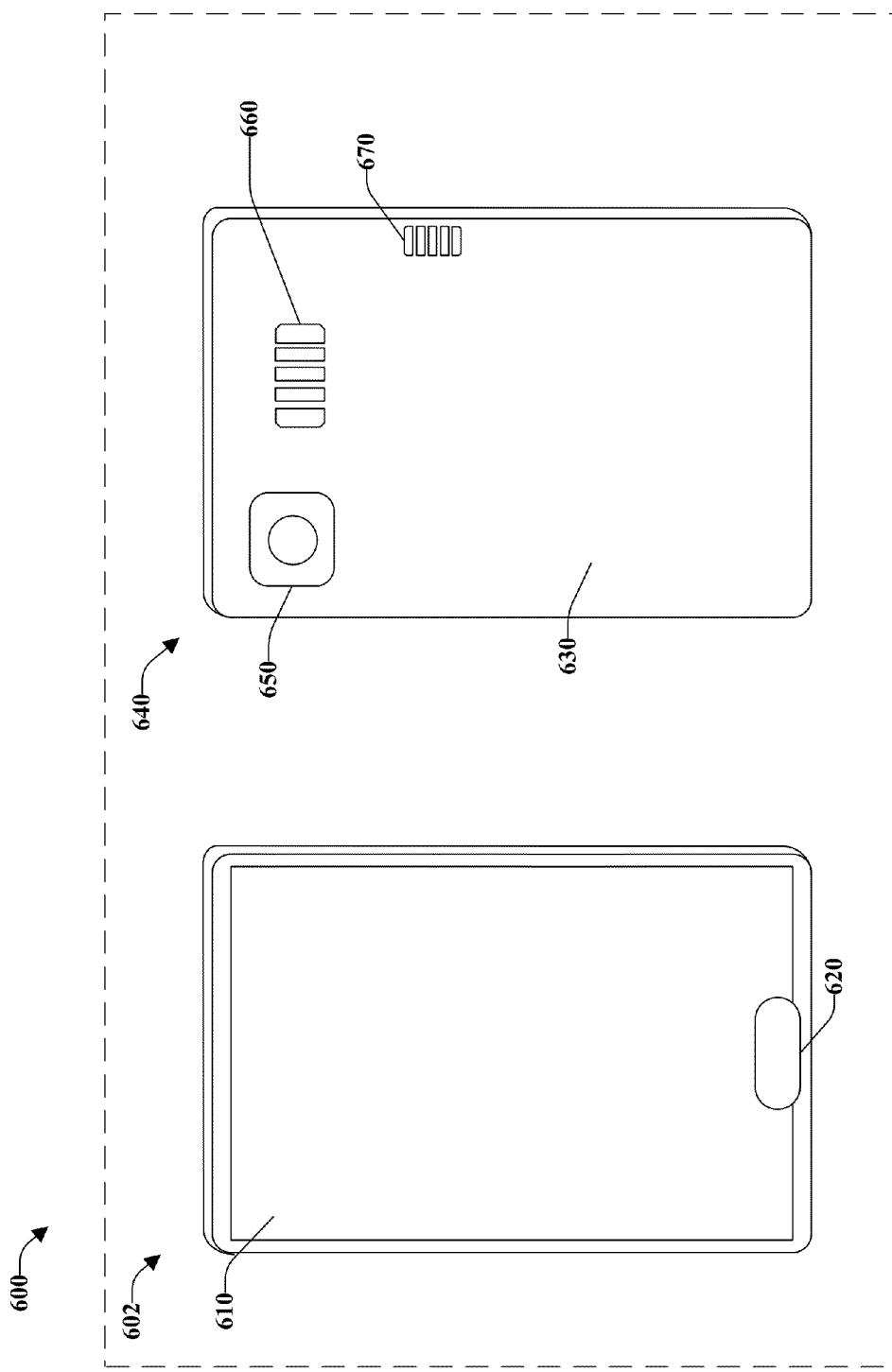
FIG. 6 illustrates a schematic diagram of an external view of an example system comprising a mobile electronic nose device in accordance with various aspects disclosed herein.

Turning now to FIG. 6, there illustrated is an exemplary schematic diagram of a system 600. System 600 can comprise a mobile device in accordance with this disclosure, as seen from a front view 602 and a back view 640. The mobile device includes a display 610, a microphone 620, a housing 630, a camera 650, a first at least one opening 660 and a second at least one opening 670.

Housing 630 comprises a shell or enclosure that houses various components in accordance with the claimed subject matter. Housing 630 can be made of a unitary or multi-piece construction and can consist of one or more of metal, glass, plastic, ceramic, polymer, wood, and other material known in the art.

In one aspect, display 610 can be a touch screen, monitor, digital display, and or other screen as known in the art. Display 610 can receive input from a user in accordance with various aspects of this specification. For example, display 610 can receive input regarding a sample of an odor, airborne gas or chemical and can receive commands through user interaction.

In one implementation, microphone 620 can receive user input. For example, microphone 620 receives audio from a user such as "identify this flower". Various components in this disclosure can receive captured input, for example, an identification component can receive a captured image.

In another aspect, camera 650 can receive and or capture visual input. For example, camera 650 can be pointed at a source object. Camera 650 can capture an image or images of the source object. Various components in this disclosure can receive captured input, for example, an identification component can receive a audio input In another aspect, the first at least one opening 660 can serve as an opening for a speaker, a heat ventilation and/or an intake for a sample delivery component in accordance with various aspects of this disclosure. In one implementation, the first at least one opening 660 comprises a plurality of slits, openings, or apertures in housing 630.

Similarly, the second at least one opening 670 can serve as an opening for a speaker, a heat ventilation and/or an outtake for a sample delivery component in accordance with various aspects of this disclosure. In one implementation, second at least one opening 670 comprises a plurality of slits, openings, or apertures in housing 630.

In another implementation, the first at least one opening 660 and the second at least one opening 670 can comprise the same at least one openings. Thus, the amount of openings can be reduced.

Referring now to FIGS. 7-9 and 13, there are illustrated methodologies and/or flow diagrams in accordance with the disclosed subject matter. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer readable device or storage medium. In another aspect, the methodologies described by FIGS. 7-9 and 13 can be facilitated by various embodiments described herein, such as those associated with FIGS. 1-6 and 10-12.

Figure 7:
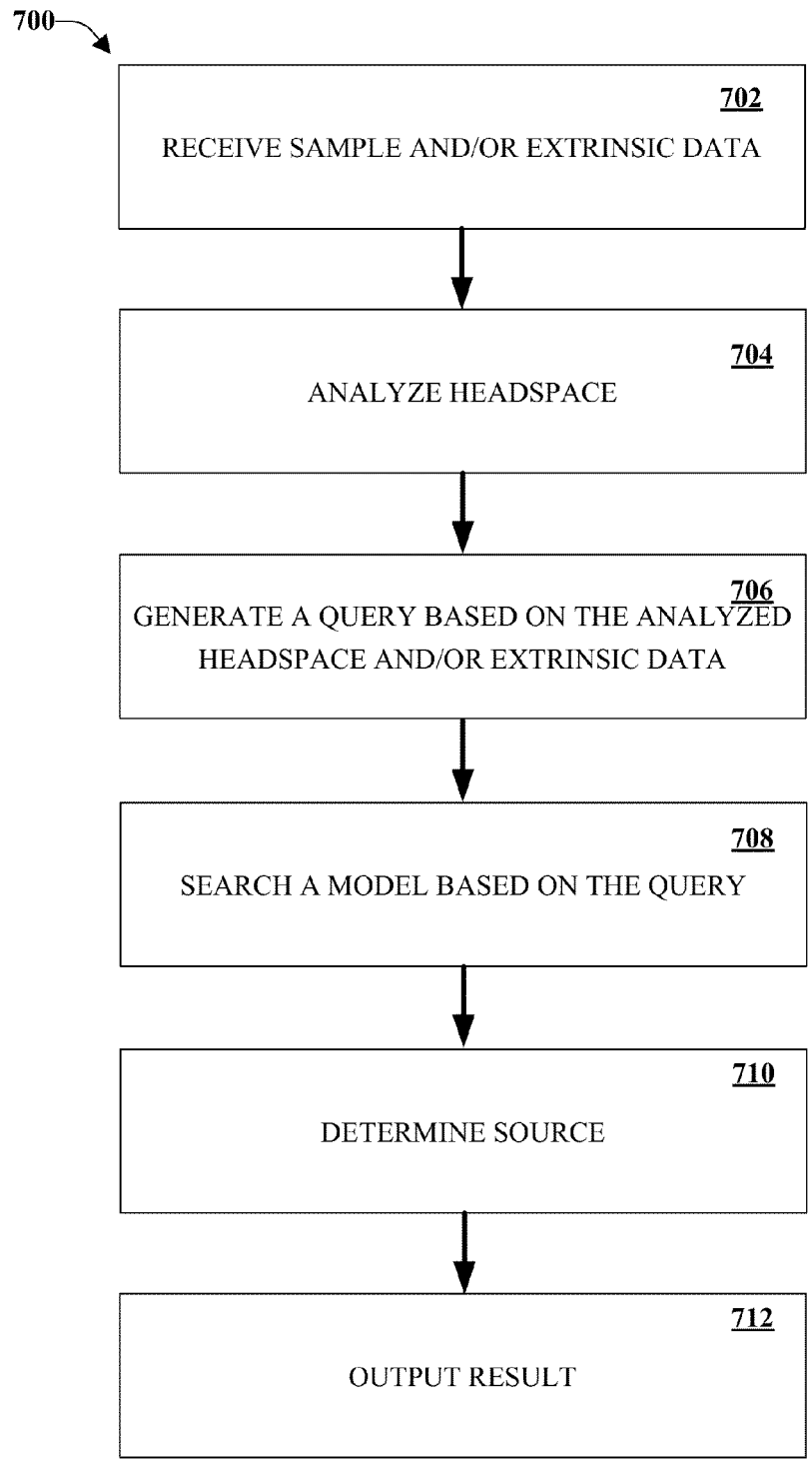
FIG. 7 illustrates an example methodology for gathering and analyzing a sample in accordance with various aspects disclosed herein.

With reference to FIG. 7, there is illustrated a methodology 700 for determining and/or identifying a source of a sample in accordance with various aspects of this disclosure. As an example, various media applications, such as, but not limited to, mobile devices such as smart phones, tablets, PDA's, cooking utensils, and cookware can use methodology 700. Specifically, methodology 700 receives a sample and identifies the sample as associated with a source.

A mobile device can receive a sample and/or extrinsic data via a sample delivery component at 702, (e.g., sample delivery component 112). For example, a fan can cause a sample to enter at least one aperture in a housing of a mobile device. In another example, a sample can passively enter at least one aperture in a housing of a mobile device at 702. In another aspect, a user can wave or move a mobile device to manually cause a sample to enter an aperture. As such, a mobile device can continuously monitor an airspace, such as to detect smoke or various chemical compounds in an airspace. In various embodiments, the extrinsic data can describe features associated with a sample or a source, capture conditions associated with a sample or source, user input, and the like.

At 704, a headspace of the sample can be analyzed by a detection component, for example. Analysis of a headspace can include a visual, a chemical analysis, and/or particle analysis (e.g., via a sensory array).

At 706, a system can generate a query (e.g., via search component 1020 described below) based on the analyzed headspace and/or extrinsic data. In an example, generating a query can comprise determining a set of filters to apply to the query. The filters can facilitate limiting possible results to reduce a number of potential candidate matches.

At 708, a system can search (e.g., via search component 1020) a model based on the query. For example, the system can compare representations of substances and/or compounds in the analyzed headspace with substances and/or compounds associated with entries in a memory (e.g., a library or model). In another example, the system can filter a model based on the filters represented in the query. Filtering the model can reduce available potential matches. For example, a query can instruct a search engine to search of a plant that blooms during July in California. The search engine can reduce potential candidate matches to plants meeting the above criteria. In another example, once potential matches are found based on comparison of representations of headspaces, the system can further search matches based on pattern recognition of an image comprise in the query (e.g., compare an image with stored images).

At 710, the source associated with the headspace can be identified via a detection component, such as detection component 120. In an aspect, a result of the search of a model can generate a set of candidate matches, confidence scores of the candidate matches, or other data associated with candidate matches. For example, a hash table analysis can result in one or more entries being associated with the headspace, background data associated with entries, and the like.

At 712, the identified source can be output as a result via an output component, such as output component 250. The output result can include a name of a source or sources, images of a source or sources, confidence scores, background information associated with the source(s), and/or additional associated information. The additional associated information can include genes, definition, common location, and the like. It is noted that the result can be received by a mobile device, rendered via an interface, stored in a memory, and the like. In another aspect, a result can be added to a model or library and/or utilized to alter a model or library (e.g., train a model).

Figure 8:
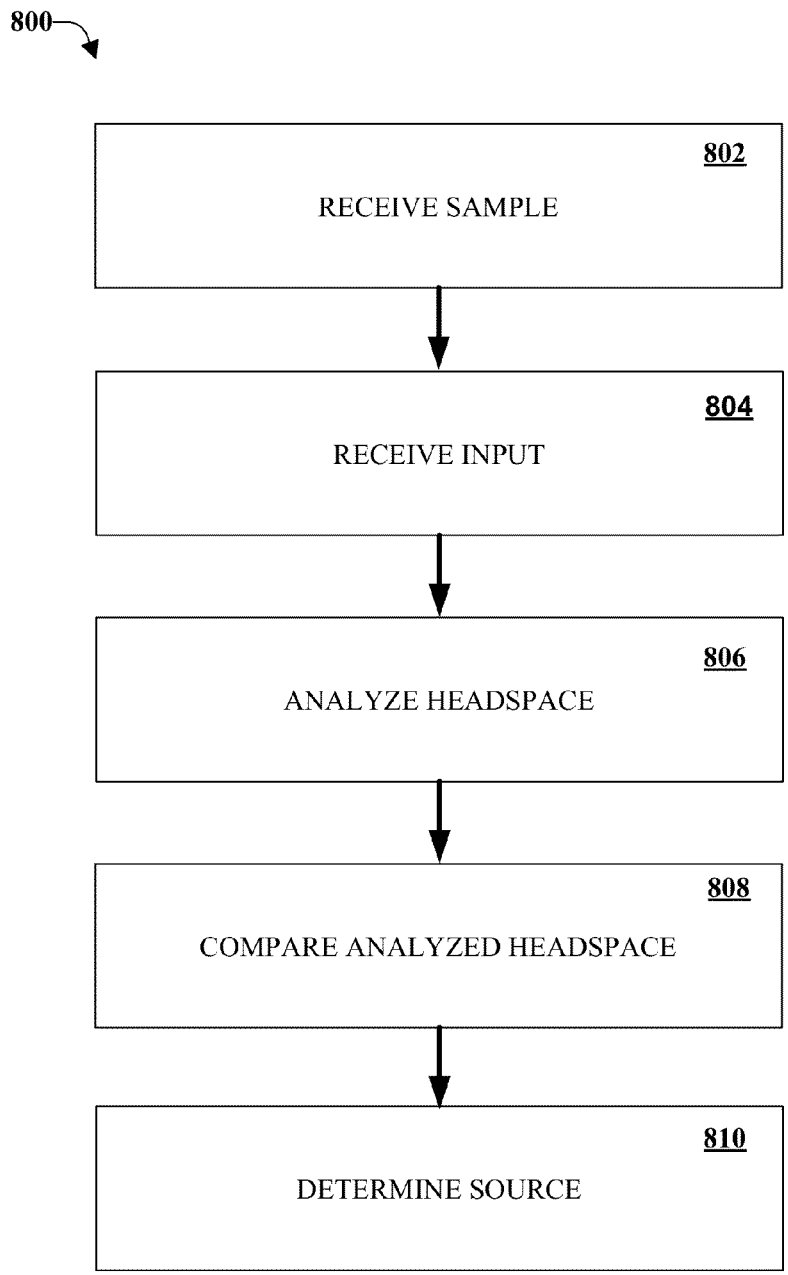
FIG. 8 illustrates an example methodology for gathering and analyzing a sample including receiving input and analyzing a sample with the received input in accordance with various aspects disclosed herein.

Turning now to FIG. 8, there is illustrated a methodology 800 for determining and/or identifying a source of a sample in accordance with various aspects of this disclosure. As an example, various media applications, such as, but not limited to, mobile devices such as smart phones, tablets, PDA's, cooking utensils, and cookware can use methodology 800. Specifically, methodology 800 receives a sample and identifies the sample as associated with a source with use of additional input.

At 802, a sample is received via a sample delivery component (e.g., sample delivery component 112). For example, a fan can cause a sample to enter at least one aperture in a housing of a mobile device. In another example, a sample can passively enter at least one aperture in a housing of a mobile device at 802. As such, a mobile device can continuously monitor an airspace, such as to detect smoke or various chemical compounds in an airspace.

At 804, input is received and/or captured via one or more input component(s), such as display 610, a microphone 620, a housing 630, and/or a camera 650. Input can comprise multiple inputs such as but not limited to user input, captured image, location information, date information, and captured audio.

At 806, a headspace of the sample and input are analyzed by a detection component, such as detection component 120, for example. In one aspect, analysis of a headspace can include a visual analysis and/or a chemical analysis (e.g., via a sensory array). In another aspect, analysis of input can include audio analysis, text analysis, image analysis, location and date analysis, for example.

At 808, the analyzed headspace and the analyzed input are compared with entries in a memory, such as memory 114, for example. Comparison can include reducing possible sources to a set of possible sources via analyzed input, such as through a hash table, fuzzy logic and the like, via components executed by a CPU, such as CPU 130. In another aspect, the analyzed headspace can be compared to the reduced set of possible sources.

At 812 a source or set of sources of the sample is determined, via a detection component, for example. In one aspect, the source or set of sources can be associated with the analyzed sample and the analyzed input. The association can be stored in memory, such as memory 114, for example.

Figure 9:
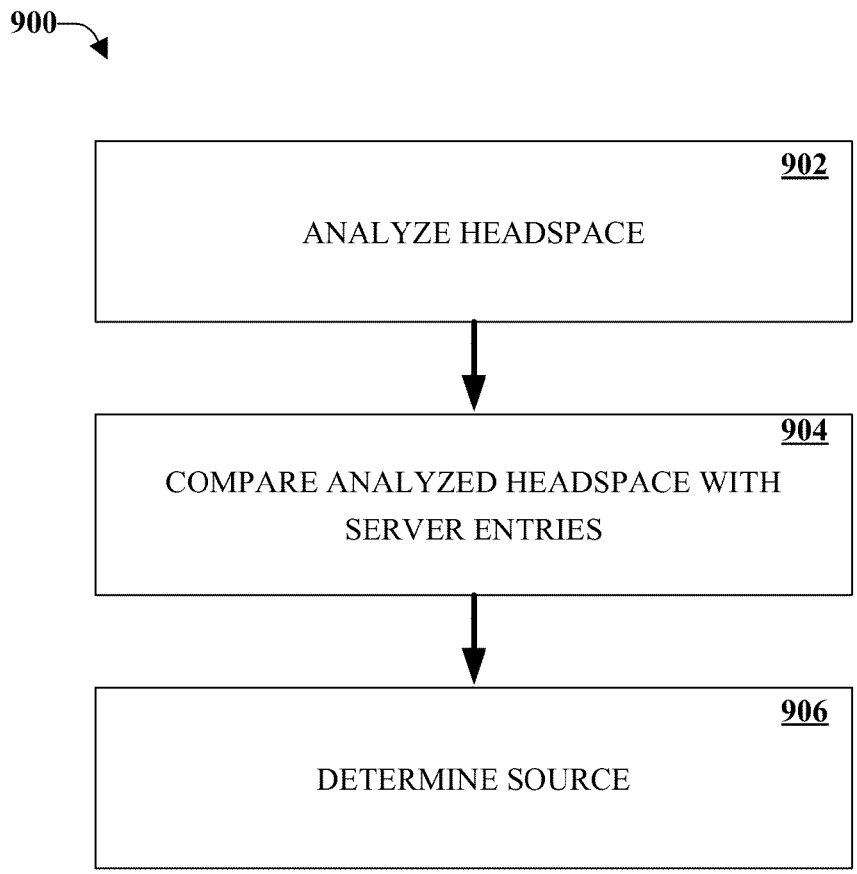
FIG. 9 illustrates an example methodology for determining a source of a sample including connecting to a server in accordance with various aspects disclosed herein.

Turning now to FIG. 9, there is illustrated a methodology 900 for determining and/or identifying a source of a sample in accordance with various aspects of this disclosure. As an example, various media applications, such as, but not limited to, mobile devices such as smart phones, tablets, PDA's, cooking utensils, and cookware can use methodology 900. Specifically, methodology 900 receives a sample and identifies the sample as associated with an entry in a data store.

At 902, a headspace of a received sample is analyzed, (e.g. by detection component 120). Analysis of a headspace can include a visual analysis and/or a chemical analysis (e.g., via a sensory array).

At 904, can analyzed headspace can be compared with entries in a server, such as server 360. In one aspect, the server can comprise a memory. The memory can contain a set of entries. Each entry of the set of entries can comprise a number of fields, such as a source name, source id, date range, location, genera, genus, class, image and the like.

At 906, a source can be determined as associated with the analyzed headspace. In one aspect, a set of source can be determined as possible sources associated with the analyzed headspace.

Turning now to FIG. 9, there is illustrated a methodology 1300 for training a library or model in accordance with various aspects of this disclosure. A system can implement methodology 1300 can receive a representation of a headspace and extrinsic data. The system can update a library based on the representation of the headspace and extrinsic data. For example, a model (e.g., library) can be trained based on gathered data and the model can be utilized to generate results to queries.

At 1302, a system can receive (e.g., via sample delivery component 312 and/or an input component 326) a signature of a headspace and extrinsic data. The signature can represent a determined composition of at least a portion of the headspace. In another aspect, the extrinsic data can comprise user input, images, locations, dates, times, and the like.

At 1304, a system can search (e.g., via search component 1020) a library based on the signature of the headspace and the extrinsic data. For example, a system can generate filters based on extrinsic data and apply the filters and the signature of the headspace to generate a query. The query can be transmitted to a search engine (e.g., search component 1020 or other search engine) that can search a model and identify a potential match(es). In an aspect, the system can determine confidence scores of the matches.

At 1306, a system can alter (e.g., via inference component 1024 described below) the library based on a result of the search, the signature of the headspace, or the extrinsic data. For example, the system can alter a stored signature of a best match. An altered signature can be generated such that the received signature is encompassed by the best match. In another example, if no match is found or no match exceeds a confidence score, then the signature can be identified as a new entry. In another aspect, the extrinsic data can be added to one or more entries to facilitate altering a library. As more entries are added and/or entries are altered, a library can become more robust and/or generate matches having higher confidence scores.

The systems and processes described below can be implemented within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders that are not all of which may be explicitly illustrated herein.

Figure 10:
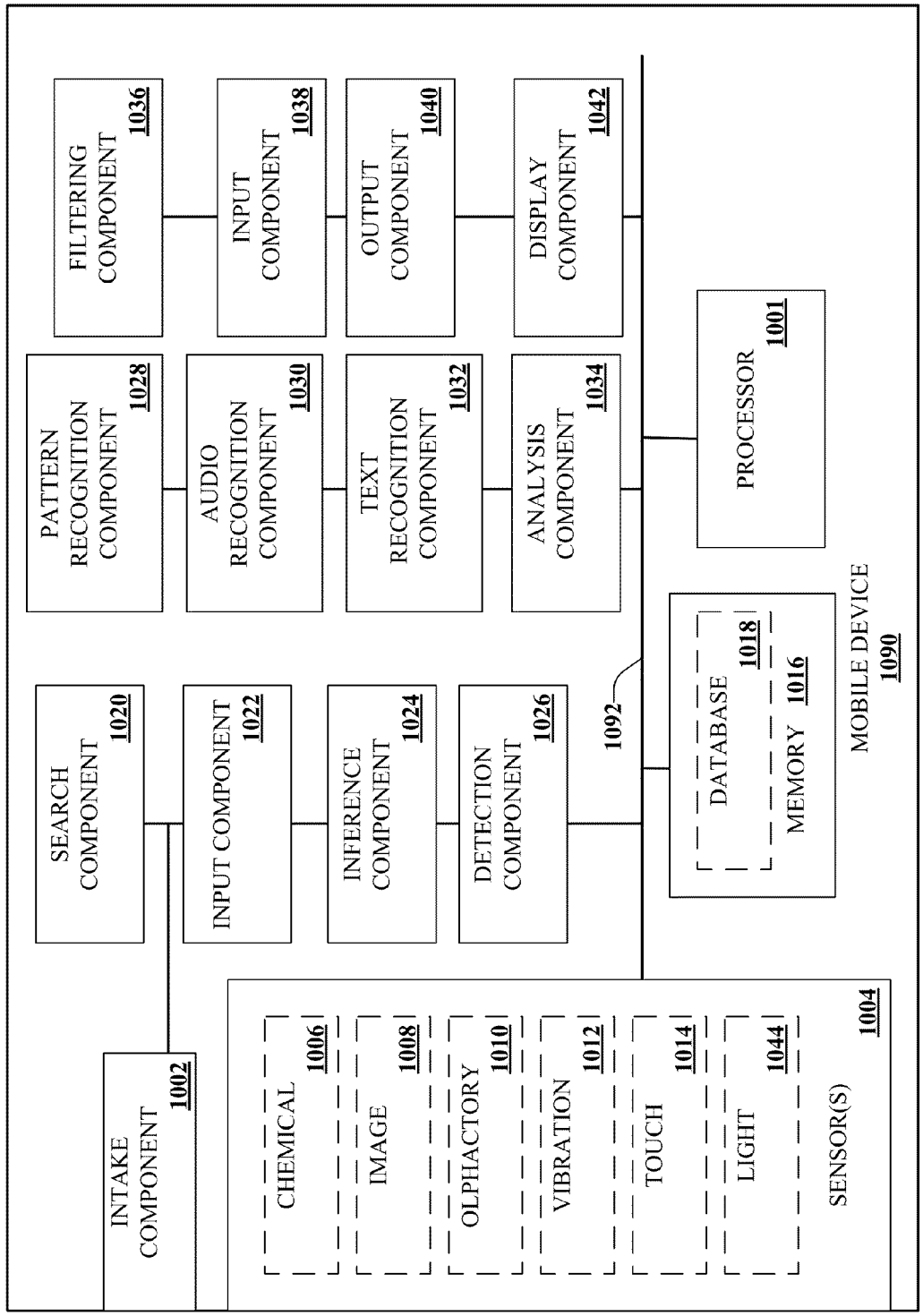
FIG. 10 illustrates a high-level functional block diagram of an example mobile electronic nose device in accordance with various aspects disclosed herein.

FIG. 10 illustrates an embodiment of a system 1000. System 1000 can comprise a mobile device 1090 (e.g., personal digital assistants (PDAs), audio/video devices, mobile phones, MPEG-1 Audio Layer 3 (MP3) players, personal computers, laptops, tablets, etc.) that includes various optional components in connection with functionalities disclosed herein. The mobile device 1090 includes a system bus 1092 connected to a processor 1001 and memory 1016. The components can be electrically and/or communicatively coupled to one another to perform various functions. An intake component 1002 collects a sample (e.g., air, gas, vapor, . . . ) in connection with electronic olfactory-based identification thereof. The intake component can passively collect samples or actively (e.g., employment of a fan, suction, MEMs device, negative pressure, or any other suitable means for collection a sample). A set of sensors 1004 sense properties associated with the sample or inputs to the device 1000. The sensors 1004 can optionally include any one or more of the following: chemical sensor 1006, image sensor 1008, olfactory sensor 1011, vibration sensor 1012, or touch sensor 1014. It is to be appreciated that other suitable sensors can be employed in connection with device 1000.

Search component 1020 can be employed to allow a user to search for information, e.g., via the Internet, to augment identification of a sample. In an aspect, the search results can be ordered as a function of relevancy to the search criteria, relevancy to user preferences, or rankings associated with the search results. The search component 1020 can be implemented on a manual basis (e.g., user input), or in an automated manner. For example, the search component 1020 can regularly or constantly run searches (e.g., in the background to generate content that is relevant to a user at a current point in time).

An input component 1022 can receive information about a source (e.g., of a smell). A detection component 1026 can detect presence and amount of chemicals in the headspace, e.g., collected by the sensors 1004. The sensors 1004 can react to various chemicals within a headspace. The reaction can cause a change in physical or electrical properties of respective sensors. In one example, absorption of the chemicals in the headspace causes physical alterations of various sensors in the set of sensors. Each sensor can react differently to the various chemicals. The processor 1001 can transform the reactions of the sensory array into a digital signal. For example, the digital signal can be computed based on a statistical model. In one non-limiting embodiment, an organic ultra-thin transistor chemical sensor having a channel that consists of one or a few monolayers can be employed. The organic thin film transistor chemical sensors can have nearly monolayer thin film channels that act as highly-sensitive detectors of trace levels of organic vapors and can perform quantitative vapor analysis. The organic ultra-thin film can be permeable to a chemical analyte of interest.

An inference component 1024 can infer actions or conclusions in connection with identification of a source or compound associated with a gather sample. As used herein, the term "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. The inference component can perform a utility-based analysis in connection with making an inference. For example, the cost of making an incorrect inference can be weighed against the benefit of making a correct inference.

Detection component 1026 can analyze chemical composition of a sample or analyze a visual aspect of the sample. Pattern recognition component 1028 can identify images captured by the device (e.g., via a camera component). Audio recognition component 1030 can identify sources of audio received by the device. The device also includes a text recognition component 1032. An analysis component 1034 analyzes information received from other components and can perform an analysis in connection with identifying source, smell, attribute, feature, composition, or the like associated with a sample.

Filtering component 1036 can employ and filter information to facilitate quickly converging on identification of source, smell, attribute, feature, composition, or the like in connection with a sample. For example, null items or features can be ruled out as potential candidates in connection with determining identification. Input component 1038 receives input, e.g., from a user. The input component 1038 can receive for example, text, typed input, verbal or audio input, image input, gesture input, or any suitable type of input for inputting information. Output component 1040 outputs results of the analyses performed herein. Display component 1042 displays results of the analyses.

Various example embodiments are disclosed below to illustrate exemplary applications and/or functions of system 1000. It is appreciated that the variations of the various embodiments can be utilized in other applications. As such, the exemplary embodiments are for illustrative purposes and are not comprehensive of all envisioned embodiments.

In various embodiments, search component 1020 can generate queries for determining one or more features of a headspace or portion of a headspace. The queries can be utilized by a local search engine or inference component 1024 to generate a result. In another example, the query can be transmitted (e.g., via output component 1040) to a remote search engine and the remote search engine can generate a result based on the query. It is noted that certain acts described in connection with detection component 1026 can be performed by a detection component remotely connected to mobile device 1090 (e.g., e.g., such as a detection component of a server device) or a search engine residing at least in part on a remote device.

In an embodiment, search component 1020 can train a machine learning system to identify smells (e.g., sources of a sample). In an aspect, a model can be trained using any number of samples that are analyzed by humans. For example, users can provide input identifying a source of a sample. For iterations of a user identifying a smell, the smell can be stored in one or more databases. The iterations can be utilized to train a model (e.g., generate a library of smells). The model can increase in size, robustness, and/or accuracy as user input increases. In an aspect, a number of identifiable smells (e.g., representations of samples match with a source) can continue to grow indefinitely.

In one or more embodiments, an initial model can be a pre-trained or seeded model that, once launched on a local device (e.g., mobile device 110), can continue with its training on a per user/device basis. In an aspect, the model can be customized per owner. It is noted that a customized (e.g., per user or group of users) model can be stored locally or remotely (e.g., cloud based storage. In some embodiments, a local model data (e.g., of mobile device 110) can be shared with a server to enhance a server model/library. It is noted that a user can provide input to opt-out of sharing a model.

In an embodiment, search component 1020 can utilize extrinsic information to reduce a number of possible results (e.g. sort known scents). As described herein, extrinsic information can include virtually any information associated with capturing a scent and/or user input. For example, extrinsic information can comprise data describing a condition associated with capturing (e.g., receiving, gathering, etc.) a sample, such as locations, GPS coordinates, seasons (e.g., season of a year), time, date, user input (e.g., voice, text, etc.), images, and the like. The extrinsic information can be utilized to In embodiments, filtering component 1036 can generate filters based on the extrinsic data. The filters can be utilized to generate a search query (e.g., via search component 1020) that is targeted to a particular species. In another example, the filters can facilitate generating a result based on a user's desire. For example, a filter can comprise data indicating the user desires to locate a retail store associated with a scent. In an example, a user can provide a voice command, textual query, or the like that indicates that the user desires to identify a scent based on a species associated with a source. Search component 1020 can then generate a query (e.g., to query a search engine) that facilitates limiting a search to a set of candidate scents belonging to the desired species or a set of possible results such as locations, suggestions, cures, and the like.

In another aspect, search component 1020 can further limit candidate scents based on additional extrinsic information. For example, filter component 1036 can determine a current location (e.g., a restaurant), date, and time and search component 1020 can apply the current location, date, and time (e.g., as filters) to generate a query that further limits potential candidate scents. In another example, a user can provide a command "identify this food." Filter component 1036 can generate a filter(s) based on the species, a current location, a time, and/or other extrinsic information. Selection component 1020 can apply the filter(s) to generate a query that is bound by the filter(s). For example, selection component 1020 can generate a query that is limited to a food, a location, and a time. The query can be utilized by search component 1020 (and/or transmitted to a search engine) to generate a result. In an example, the search engine can limit potential results to restaurants near the current location of mobile device 1090 and to food available at the restaurants at the time. In one aspect, a current location of the mobile device 1090 can be determined based on GPS location, a local access point, other devices, and the like. It is noted that the above is but a limited set of examples; as such, search component 1020 can utilize virtually any criterion (extrinsic data) or combination of criteria to limit candidate scents, improve accuracy, decrease processing time, or otherwise alter performance.

As another example, a user can identify a smell and system 1000 can collect a headspace, perform an analysis (e.g., locally or through a cloud-based analysis), and apply filters to facilitate proper identification of sources, scent signature matches, and generation of an identified source. In some embodiments, system 1000 can generate or receive a confidence score and provide the confidence score to a user (e.g., 99% confident that a scent includes garlic and onion). A confidence score can be determined based on matching a representation of the headspace and/or extrinsic data to a model. In one aspect, the confidence score can be a weighted confidence score that assigns weights based on the representation of the headspace, extrinsic data, user profiles, and the like.

In one or more embodiments, system 1000 can be configured to perform specialized functions or limited detection of substances. In an aspect, system 1000 can be pre-configured to identify a number of scents based on constraints generated by filter component 1026. As noted above, the constraints can be generated based on a detection mode or the like.

In one example, a user can trigger a particular mode or a mode can be entered automatically. For example, a user can trigger entering an allergy mode or an allergy mode can be entered based on detecting a trigger, such as a sneeze. In an aspect, an allergy mode can facilitate filter component 1036 generating filters that facilitate, when applied by search component 1020, limiting identifying a source associated with a headspace and providing a list of possible allergens. In accordance with various embodiments disclosed herein, detection component 1026 can store identified sources and compare the identified sources to determine a common possible allergen. In another example, filter component 1036 can utilize extrinsic information (e.g., location, date, time, etc.) to generate filters that limit results to possible allergens. In another aspect, search component 1020 can generate a query based on the extrinsic data and a remote search engine can generate a result. The result can be received by input component 1038 and displayed by display component 1042.

In various embodiments, inference component 1024/or a remote search engine can determine results to search queries comprising a solution, warning, suggestion, or other descriptive data associated with a scent based on identification of substances and/or extrinsic information. For example, a user can take a picture of source and/or utter a command to identify the chemical makeup of the source (e.g., snaps a picture of a blade of a weed and utters identify this weed). Pattern recognition component 1028 can recognize an object (e.g., based on pattern recognition techniques) and audio recognition component 1030 can recognize a command based on the user uttering the command. The combination of pattern recognition, audio recognition, and headspace analysis can facilitate filtering component 1036 generating one or more filters to limit a search by search component 1020. In an aspect, search component 1020 can generate a query to search a model and a result can accurately identify the type of plant as well as provide supplemental information regarding allergic properties, best ways of eradicate the weed, potential harmful or beneficial properties, or the like.

In another embodiment, a search engine and/or inference component 1024 can provide a potential solution based on matched entries in a model. For example, radon gas, leaking oil or gas, or other chemicals, body odor, foot odor, type of bacteria associated with particular odors can be detected and solutions to kill such bacteria can be generated. In another example, a result can comprise an alert. In an aspect, the alert can be an audio notification, visual notification, vibration, or the like. For example, if a pathogen is detected and the pathogen has a high concentration (e.g., above a certain threshold) the mobile device 1090 can generate an alert (e.g., via display component 1042) indicating the high concentration of the pathogen.

In another embodiment, inference component 1024 can determine a direction of a scent and can determine a navigational path to a likely source of the scent. It is noted that inference component 1024 can include an accelerometer, gyroscope, GPS component, or the like. In some embodiments, intake component 1002 can receive or gather multiple samples to determine a location or direction of a scent. For example, a user can walk in an environment and smell food, such as a barbeque scent, which the user desires to locate. Sample delivery intake component 1002 can gather samples as a user moves and detection component 1026 can determine whether a concentration of the scent is altered (e.g., increase or decreased). In one aspect, intake component 1002 can gather samples periodically (e.g., based on passage of time, distance traveled), randomly, semi-randomly, based on user commands, or the like. As samples are gathered and/or analyzed, the concentrations of a scent can be utilized to determine a direction for a user to travel in order to locate the scent. For example, if a concentration or intensity is increasing, the user may be traveling in the proper direction. In another example, a user can smell some foul odor in a building or other environment. The user can utilize mobile device 1090 to detect the location of the foul smell and remove the smell (e.g., spoiled food, rotten garbage, and the like).

In an implementation, mobile device 1000 can share models (e.g., libraries) and/or utilize models in a cloud-computing environment. For example, mobile device 1000 can share (e.g., transmit) a local library to other mobile devices or servers. In an aspect, multiple libraries can be aggregated and a robust library can be generated. In some embodiments, a library can be based in part on extrinsic data such a location, date, time, images, and the like. For example, every time mobile device 1000 gathers a sample, location data (e.g., GPS location, date, time, etc.) can be recorded and/or attached to a model. Inference component 1024 can monitor location data can be matched with other location data to provide a more detailed and/or improved model.

In an aspect, a library can be queried to determine candidate matches based on a representation of a headspace or extrinsic data. In one or more embodiments, searching can comprise comparing entries in a library to determine a confidence score associated with entries of the library. The confidence score can be based on a level of match of representations of headspaces and extrinsic data. In one example, entries can be stored as nodes of a hash table. Unique hashes or signatures can be assigned to different entries of the hash table. It is noted that the signatures can be based on representations of headspaces. In another aspect, each entry can be associated with extrinsic data (e.g., images, locations, dates, etc.). In other examples, signatures can be based on representations of headspaces in combination with extrinsic data. In another embodiment, inference component 1024 can updated and/or generate models based on a monitor history and/or results.

Figure 11:
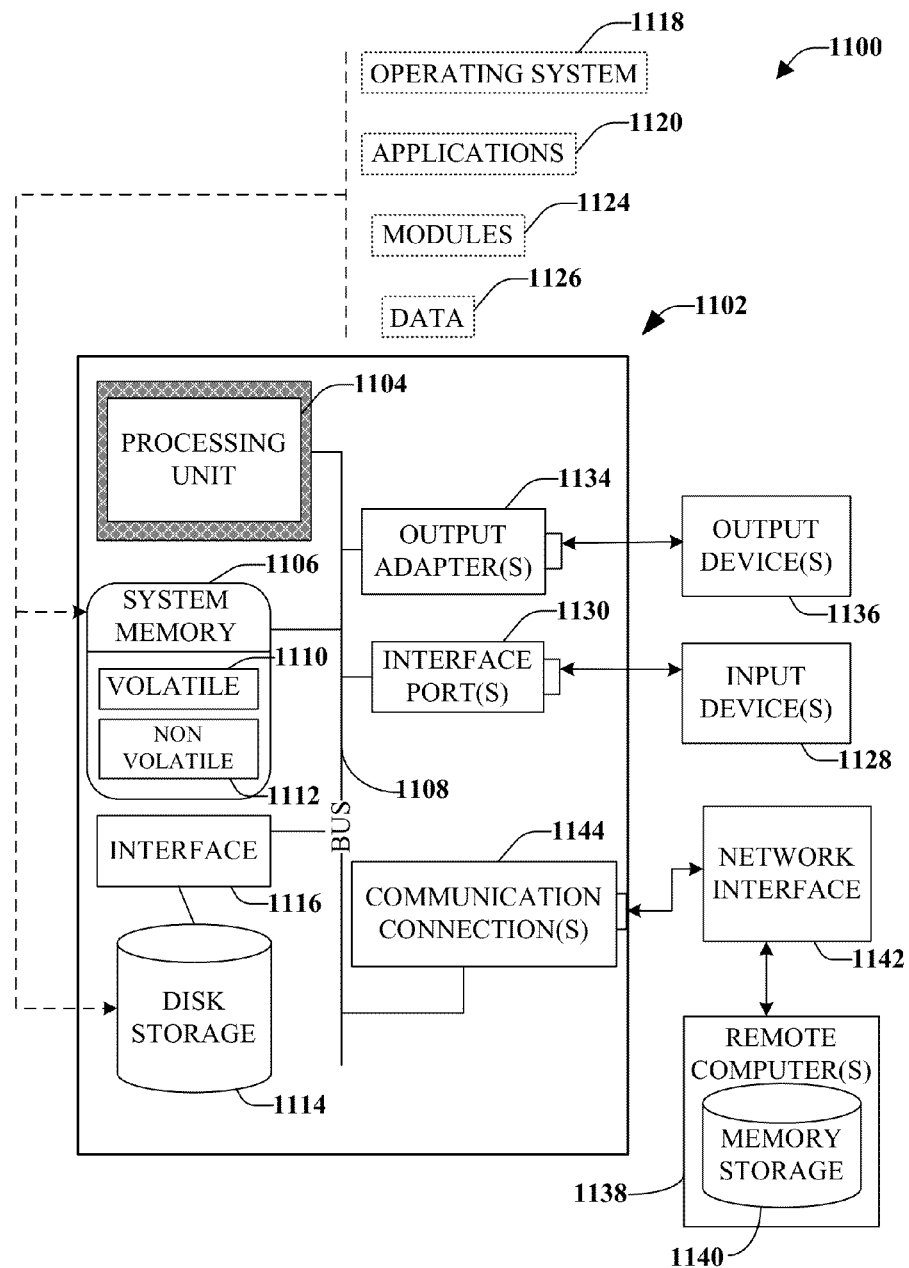
FIG. 11 illustrates an example schematic block diagram of a computing environment in accordance with this specification in accordance with various aspects disclosed herein.

With reference to FIG. 11, a suitable environment 1100 for implementing various aspects of the claimed subject matter includes a computer 1102. The computer 1102 includes a processing unit 1104, a system memory 1106, a codec 1105, and a system bus 1108. The system bus 1108 couples system components including, but not limited to, the system memory 1106 to the processing unit 1104. The processing unit 1104 can be any of various available processors. Dual microprocessors and other multiprocessor architectures also can be employed as the processing unit 1104.

The system bus 1108 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCM-CIA), Firewire (IEEE 1394), and Small Computer Systems Interface (SCSI).

The system memory 1106 includes volatile memory 1111 and non-volatile memory 1112. The basic input/output system (BIOS), containing the basic routines to transfer information between elements within the computer 1102, such as during start-up, is stored in non-volatile memory 1112. By way of illustration, and not limitation, non-volatile memory 1112 can include read only memory (ROM), programmable ROM (PROM), electrically programmable ROM (EPROM), electrically erasable programmable ROM (EEPROM), or flash memory. Volatile memory 1111 includes random access memory (RAM), which acts as external cache memory. According to present aspects, the volatile memory may store the write operation retry logic (not shown in FIG. 11) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM).

Computer 1102 may also include removable/non-removable, volatile/non-volatile computer storage media. FIG. 11 illustrates, for example, a disk storage 1114. Disk storage 1114 includes, but is not limited to, devices like a magnetic disk drive, solid state disk (SSD) floppy disk drive, tape drive, Zip drive, LS-110 drive, flash memory card, or memory stick. In addition, disk storage 1114 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1114 to the system bus 1108, a removable or non-removable interface is typically used, such as interface 1116.

It is to be appreciated that FIG. 11 describes software, software in execution, hardware, and/or software in combination with hardware that acts as an intermediary between users and the basic computer resources described in the suitable operating environment 1100. Such software includes an operating system 1118. Operating system 1118, which can be stored on disk storage 1114, acts to control and allocate resources of the computer system 1102. Applications 1120 take advantage of the management of resources by operating system 1118 through program modules 1124, and program data 1126, such as the boot/shutdown transaction table and the like, stored either in system memory 1106 or on disk storage 1114. It is to be appreciated that the claimed subject matter can be implemented with various operating systems or combinations of operating systems. For example, applications 1120 and program data 1126 can include software implementing aspects of this disclosure.

A user enters commands or information into the computer 1102 through input device(s) 1128, non-limiting examples of which can include a pointing device such as a mouse, trackball, stylus, touch pad, keyboard, microphone, joystick, game pad, satellite dish, scanner, TV tuner card, digital camera, digital video camera, electronic nose, web camera, and any other device that allows the user to interact with computer 11311. These and other input devices connect to the processing unit 1104 through the system bus 1108 via interface port(s) 1130. Interface port(s) 1130 include, for example, a serial port, a parallel port, a game port, and a universal serial bus (USB). Output device(s) 1136 use some of the same type of ports as input device(s) 1128. Thus, for example, a USB port may be used to provide input to computer 1102, and to output information from computer 1102 to an output device 1136. Output adapter 1134 is provided to illustrate that there are some output devices 1136 like monitors, speakers, and printers, among other output devices 1136, which require special adapters. The output adapters 1134 include, by way of illustration and not limitation, video and sound cards that provide a means of connection between the output device 1136 and the system bus 1108. It should be noted that other devices and/or systems of devices provide both input and output capabilities such as remote computer(s) 1138.

Computer 1102 can operate in a networked environment using logical connections to one or more remote computers, such as remote computer(s) 1138. The remote computer(s) 1138 can be a personal computer, a server, a router, a network PC, a workstation, a microprocessor based appliance, a peer device, a smart phone, a tablet, or other network node, and typically includes many of the elements described relative to computer 1102. For purposes of brevity, only a memory storage device 1140 is illustrated with remote computer(s) 1138. Remote computer(s) 1138 is logically connected to computer 1102 through a network interface 1142 and then connected via communication connection(s) 1144. Network interface 1142 encompasses wire and/or wireless communication networks such as local-area networks (LAN), wide-area networks (WAN), and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1144 refers to the hardware/software employed to connect the network interface 1142 to the bus 1108. While communication connection 1144 is shown for illustrative clarity inside computer 1102, it can also be external to computer 1102. The hardware/software necessary for connection to the network interface 1142 includes, for exemplary purposes only, internal and external technologies such as, modems including regular telephone grade modems, cable modems and DSL modems, ISDN adapters, wired and wireless Ethernet cards, hubs, wireless transceivers, and routers.

Figure 12:
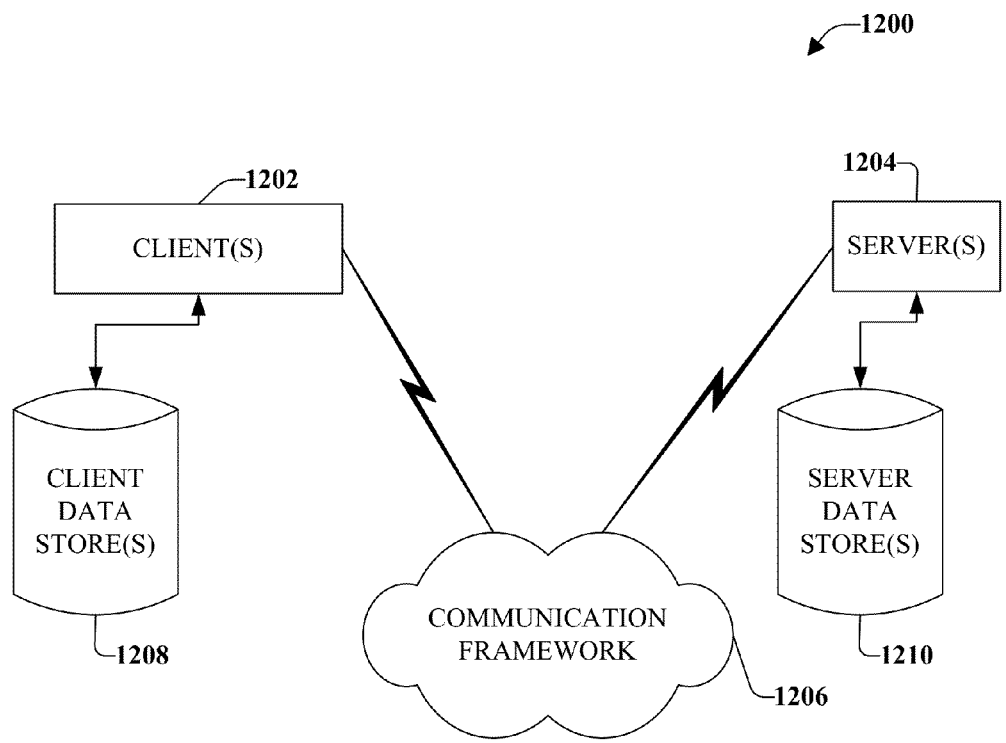
FIG. 12 illustrates an example block diagram of a computer operable to execute various implementations described herein.
Figure 13:
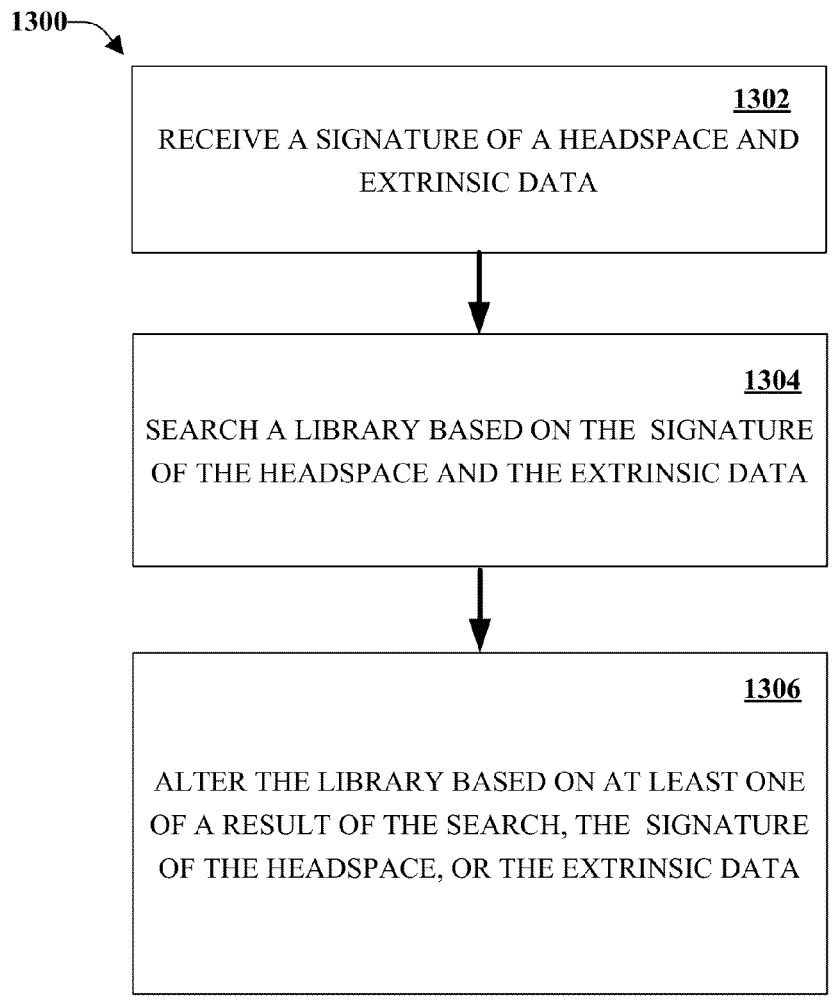
FIG. 13 illustrates an example methodology training a model in accordance with various aspects disclosed herein.

Referring now to FIG. 12, there is illustrated a schematic block diagram of a computing environment 1200 in accordance with this specification. The system 1200 includes one or more client(s) 1202, (e.g., computers, smart phones, tablets, cameras, PDA's). The client(s) 1202 can be hardware and/or software (e.g., threads, processes, computing devices). The client(s) 1202 can house cookie(s) and/or associated contextual information by employing the specification, for example.

The system 1200 also includes one or more server(s) 1204. The server(s) 1204 can also be hardware or hardware in combination with software (e.g., threads, processes, computing devices). The servers 1204 can house threads to perform transformations of media items by employing aspects of this disclosure, for example. One possible communication between a client 1202 and a server 1204 can be in the form of a data packet adapted to be transmitted between two or more computer processes wherein data packets may include coded analyzed headspaces and/or input. The data packet can include a cookie and/or associated contextual information, for example. The system 1200 includes a communication framework 1206 (e.g., a global communication network such as the Internet) that can be employed to facilitate communications between the client(s) 1202 and the server(s) 1204.

Communications can be facilitated via a wired (including optical fiber) and/or wireless technology. The client(s) 1202 are operatively connected to one or more client data store(s) 1208 that can be employed to store information local to the client(s) 1202 (e.g., cookie(s) and/or associated contextual information). Similarly, the server(s) 1204 are operatively connected to one or more server data store(s) 1211 that can be employed to store information local to the servers 1204.

In one exemplary implementation, a client 1202 can transfer an encoded file, (e.g., encoded media item), to server 1204. Server 1204 can store the file, decode the file, or transmit the file to another client 1202. It is to be appreciated, that a client 1202 can also transfer uncompressed file to a server 1204 and server 1204 can compress the file and/or transform the file in accordance with this disclosure. Likewise, server 1204 can encode information and transmit the information via communication framework 1206 to one or more clients 1202.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described herein (e.g., detection components, input components, sample delivery components, and the like) can include electrical circuit(s) that can include components and circuitry elements of suitable value in order to implement the aspects of this innovation(s). Furthermore, it can be appreciated that many of the various components can be implemented on one or more integrated circuit (IC) chips. In one exemplary implementation, a set of components can be implemented in a single IC chip. In other exemplary implementations, one or more of respective components are fabricated or implemented on separate IC chips.

What has been described above includes examples of the implementations of the present invention. It is, of course, not possible to describe every conceivable combination of components or methodologies for purposes of describing the claimed subject matter, but it is to be appreciated that many further combinations and permutations of this innovation are possible. Accordingly, the claimed subject matter is intended to embrace all such alterations, modifications, and variations that fall within the spirit and scope of the appended claims. Moreover, the above description of illustrated implementations of this disclosure, including what is described in the Abstract, is not intended to be exhaustive or to limit the disclosed implementations to the precise forms disclosed. While specific implementations and examples are described herein for illustrative purposes, various modifications are possible that are considered within the scope of such implementations and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than or equal to 11" can include any and all sub-ranges between (and including) the minimum value of zero and the maximum value of 11, that is, any and all sub-ranges having a minimum value of equal to or greater than zero and a maximum value of equal to or less than 11, e.g., 1 to 5. In certain cases, the numerical values as stated for the parameter can take on negative values.

In addition, while a particular feature of this innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Reference throughout this specification to "one implementation," or "an implementation," means that a particular feature, structure, or characteristic described in connection with the implementation is included in at least one implementation. Thus, the appearances of the phrase "in one implementation," or "in an implementation," in various places throughout this specification are not necessarily all referring to the same implementation. Furthermore, the particular features, structures, or characteristics may be combined in any suitable manner in one or more implementations.

Further, references throughout this specification to an "item," or "file," means that a particular structure, feature or object described in connection with the implementations are not necessarily referring to the same object. Furthermore, a "file" or "item" can refer to an object of various formats.

As used in this application, the terms "component," "module," "system," or the like are generally intended to refer to a computer-related entity, either hardware (e.g., a circuit), a combination of hardware and software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. While separate components are depicted in various implementations, it is to be appreciated that the components may be represented in one or more common component. Further, design of the various implementations can include different component placements, component selections, etc., to achieve an optimal performance. Further, a "device" can come in the form of specially designed hardware; generalized hardware made specialized by the execution of software thereon that enables the hardware to perform specific function (e.g., media item aggregation); software stored on a computer readable medium; or a combination thereof.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A mobile wireless communications device comprising:
a wireless transceiver;
a sample delivery component that receives a headspace sample associated with a scent; and
a processor that executes the following computer-executable components stored in a memory:
a detection component that analyzes at least a portion of the headspace sample and generates a representation of at least the portion;
a filtering component that receives at least one filtering criterion representing a filter for possible candidate matches to the representation;
a search component that:
generates a search query based on at least the representation and the at least one filtering criterion, wherein search component generates the search query to identify an animal associated with the representation of at least the portion of headspace; and
transmits the search query to a search engine; and
an input component that receives a result from the search engine, wherein the result identifies one or more features associated with the scent.

2. The device of claim 1, further comprising a pattern recognition component that identifies a pattern in an image associate with the headspace sample, wherein the search component further generates the search query based on the identified image.

3. The device of claim 1, further comprising:
an input component that receives a voice command, and wherein the search component further generates the search query based on the voice command.

4. The device of claim 1, further comprising an inference component that trains a model to identify a source of at least the portion based on a history of identifying portions of headspaces.

5. The device of claim 1, comprising an output component that generates an output that identifies types of prey or predators within an area of the device.

6. The device of claim 1, wherein:
the sample delivery component receives the headspace sample in an area that comprises an animal track; and
the search component further generates the search query based at least in part on an image of the animal track.

7. The device of claim 1, wherein the detection component determines a level of freshness of the animal track based on a concentration of at least the portion of headspace that is associated with the animal.

8. The device of claim 1, further comprising a navigation component that determines, based on a concentration of the representation of at least the portion of headspace, a direction that, when traveled, leads to the animal.

9. The device of claim 1, wherein the navigation component further determines a location of the animal based on the direction and a global positioning system.

10. The device of claim 1, wherein the detection component analyzes at least the portion of the headspace sample to detect a presence of an allergen, and the search component generates the search query based on the allergen.

11. The device of claim 1, further comprising:
an output component that renders the result, wherein the one or more features comprises at least one of a solution to eradicate a plant associated with the scent, a level of danger associated with the scent, or a possible cause of the scent.

12. A method, comprising:
employing a processor, located in a mobile device, to execute computer executable components stored in a memory to perform the following acts:
analyzing at least a portion of a headspace sample and generating a representation of at least the portion;
receiving at least one filtering criterion representing a filter for possible candidate matches to the representation;
generating a search query based on at least the representation and the at least one filtering criterion, wherein the search query is employed to identify an animal associated with the representation of at least the portion of headspace;

transmitting the search query to a search engine; and receiving a result from the search engine, wherein the result identifies one or more features associated with the scent.

13. The method of claim 12, further comprising receiving extrinsic data describing an aspect associated with capturing the headspace sample, wherein the extrinsic data describes at least one of a location of the capturing, an image associated with a potential source of the capturing, a date of the capturing, or a desired function that limits the potential source.

14. The method of claim 13, wherein the acts further comprise:

triggering the capturing of the headspace in response to detecting a triggering event, wherein the triggering event comprises at least one of a sneeze or a user exhaling.

15. The method of claim 12, further comprising generating a display to a user that identifies the animal.

16. The method of claim 15, wherein the acts further comprise:

determining a location of the animal based on directional or global positioning information.

17. A mobile phone, comprising:

a sample delivery component that gathers a headspace sample of an airborne scent; and a processor that executes the following computer-executable components stored in a memory:

a detection component that generates a representation of a detected composition of the headspace sample;

a filtering component that receives data describing a condition of the gathering the headspace sample;

a search component that queries a search engine based on the data describing the condition of the gathering and the representation of the detected composition, wherein the query is structured to identify an animal associated with the representation of the detected composition; and an input component that receives a result from the search engine, wherein the result identifies one or more features associated with the headspace sample; and an output component that generates a display identifying the animal associated with the representation of the detected composition.

18. The mobile phone of claim 17, wherein the search engine searches a specialized model, based on expert opinions, to generate the result.

19. The mobile phone of claim 17, further comprising a navigation component that determines, based on a concentration of the representation, a direction that, when traveled, leads to a source of the headspace sample.

20. The mobile phone of claim 19, wherein the navigation component generates a marker identifying a location associated with the gathering the headspace sample and at least one of a date of the receiving the headspace sample, a time of the receiving the headspace sample, or a determined concentration of the source associated with at least the portion of the headspace sample.

* * * * *